(12) United States Patent
Liepold et al.

(10) Patent No.: US 7,753,340 B2
(45) Date of Patent: Jul. 13, 2010

(54) VALVE

(75) Inventors: Gerhard Liepold, Watchung, NJ (US); Dietrich Bizer, Madison, NJ (US)

(73) Assignee: GL Tool and Manufacturing Co. Inc., Livingston, NJ (US)

( * ) Notice: Subject to any disclaimer, the term of this patent is extended or adjusted under 35 U.S.C. 154(b) by 943 days.

(21) Appl. No.: 10/566,611

(22) PCT Filed: Jul. 30, 2004

(86) PCT No.: PCT/US2004/024732
§ 371 (c)(1), (2), (4) Date: Jan. 31, 2006

(87) PCT Pub. No.: WO2005/012775
PCT Pub. Date: Feb. 10, 2005

(65) Prior Publication Data
US 2006/0243942 A1 Nov. 2, 2006

Related U.S. Application Data

(60) Provisional application No. 60/491,737, filed on Aug. 1, 2003.

(51) Int. Cl.
*F16K 31/44* (2006.01)
(52) U.S. Cl. .................. 251/252; 251/344
(58) Field of Classification Search ........... 251/251, 251/252, 341, 343, 344, 347; 137/614.15
See application file for complete search history.

(56) References Cited

U.S. PATENT DOCUMENTS

| | | | | |
|---|---|---|---|---|
| 1,387,446 A | * | 8/1921 | Antoine | 137/219 |
| 3,367,626 A | * | 2/1968 | Stern | 251/340 |
| 3,395,725 A | * | 8/1968 | Roach | 137/512.15 |
| 3,985,332 A | * | 10/1976 | Walker | 251/111 |
| 4,117,859 A | * | 10/1978 | Illy | 137/219 |
| 4,421,298 A | * | 12/1983 | Kujawski | 251/368 |
| 6,237,639 B1 | * | 5/2001 | Jougla et al. | 137/899.2 |
| 6,354,466 B1 | | 3/2002 | Karpisek | |

(Continued)

FOREIGN PATENT DOCUMENTS

AT          6 052 U      3/2003

(Continued)

*Primary Examiner*—John K Fristoe, Jr.
*Assistant Examiner*—Marina Tiet Jen
(74) *Attorney, Agent, or Firm*—Hoffman & Baron, LLP

(57) ABSTRACT

The invention provides a valve (1) for sterile transfer of fluids. The valve (1) comprises a housing (5) having first and second open ends (2, 3) and a passageway (4) extending between the ends (2, 3). The first end (2) has a flange (54) for coupling the housing (5) about an opening (205) of an external conduit (201) and a seal blocking an open area of the first end (2). The seal is placed in register with the opening (205) of the external conduit (201). The valve (1) has a piston (9) movably disposed within the housing (5) so as to interrupt the seal and to permit fluid to pass along the passageway (4). A mating surface (215) of the flange (54) and the seal form a sterilizable surface. The seal is formed between a plastic plug (18) movable by the piston (9) and a sharp plastics rim (15) which encompasses the open area of a first end (16) of the housing (5).

40 Claims, 25 Drawing Sheets

U.S. PATENT DOCUMENTS

| | | | |
|---|---|---|---|
| 6,491,283 B2 * | 12/2002 | Newberg | 251/335.2 |
| 7,370,673 B2 * | 5/2008 | Trumbower et al. | 137/883 |
| 2002/0074532 A1 * | 6/2002 | Rovira et al. | 251/129.21 |
| 2005/0121642 A1 * | 6/2005 | Purdy | 251/343 |
| 2005/0150546 A1 * | 7/2005 | Liepold et al. | 137/68.3 |
| 2006/0142730 A1 * | 6/2006 | Proulx et al. | 604/403 |

FOREIGN PATENT DOCUMENTS

| | | | |
|---|---|---|---|
| WO | WO 03/090842 | | 6/2003 |
| WO | WO 03/038322 | | 8/2003 |
| WO | WO03090842 | * | 11/2003 |

* cited by examiner

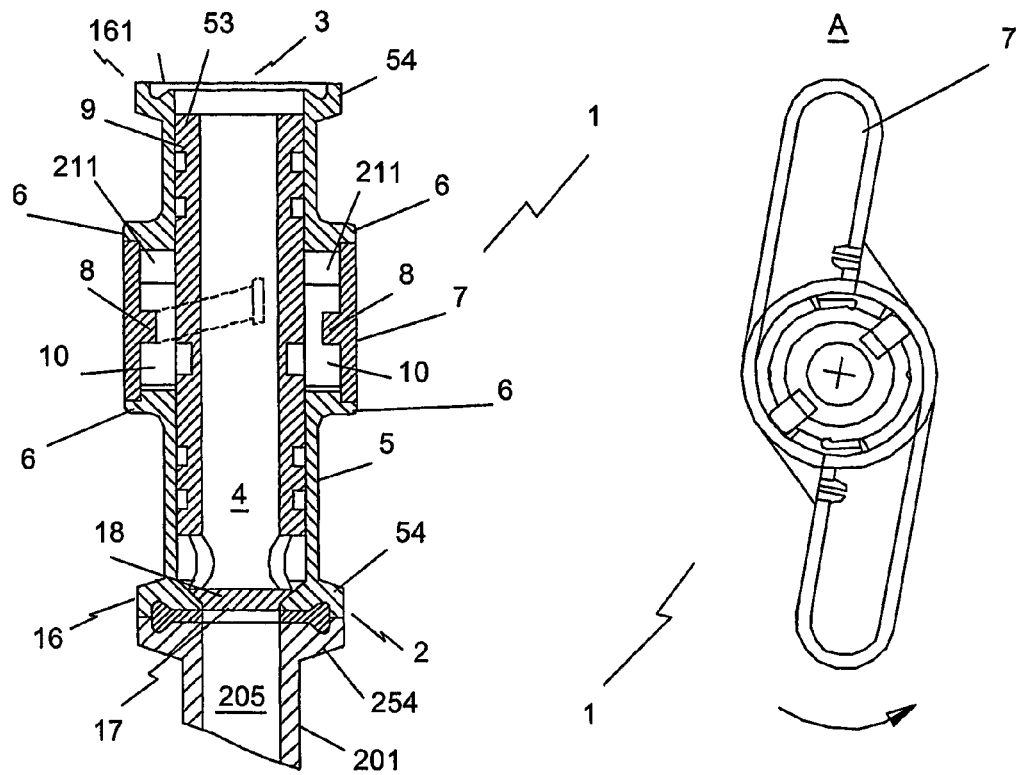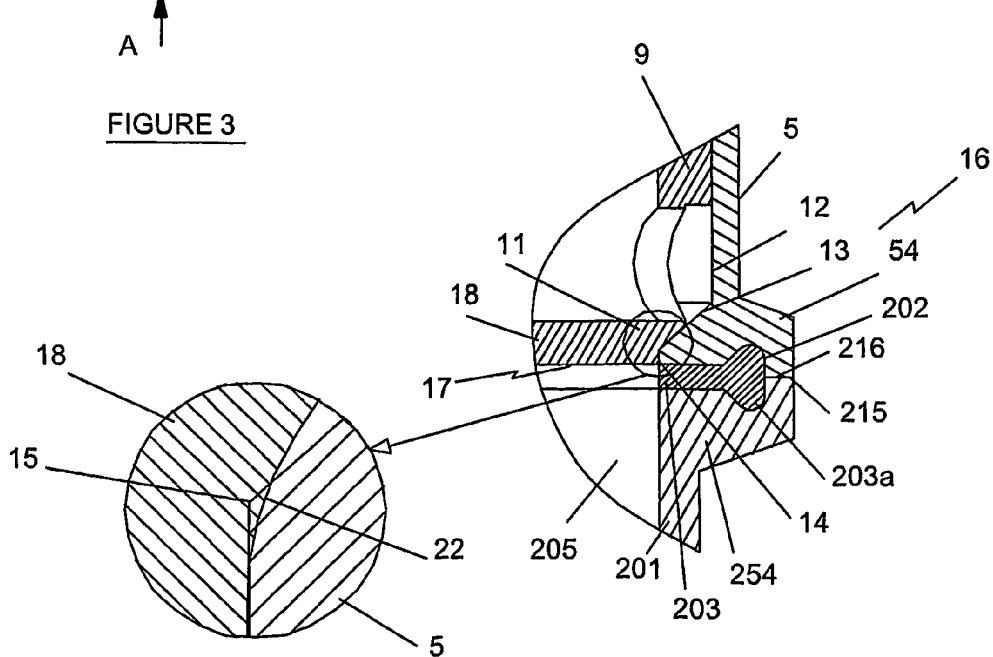

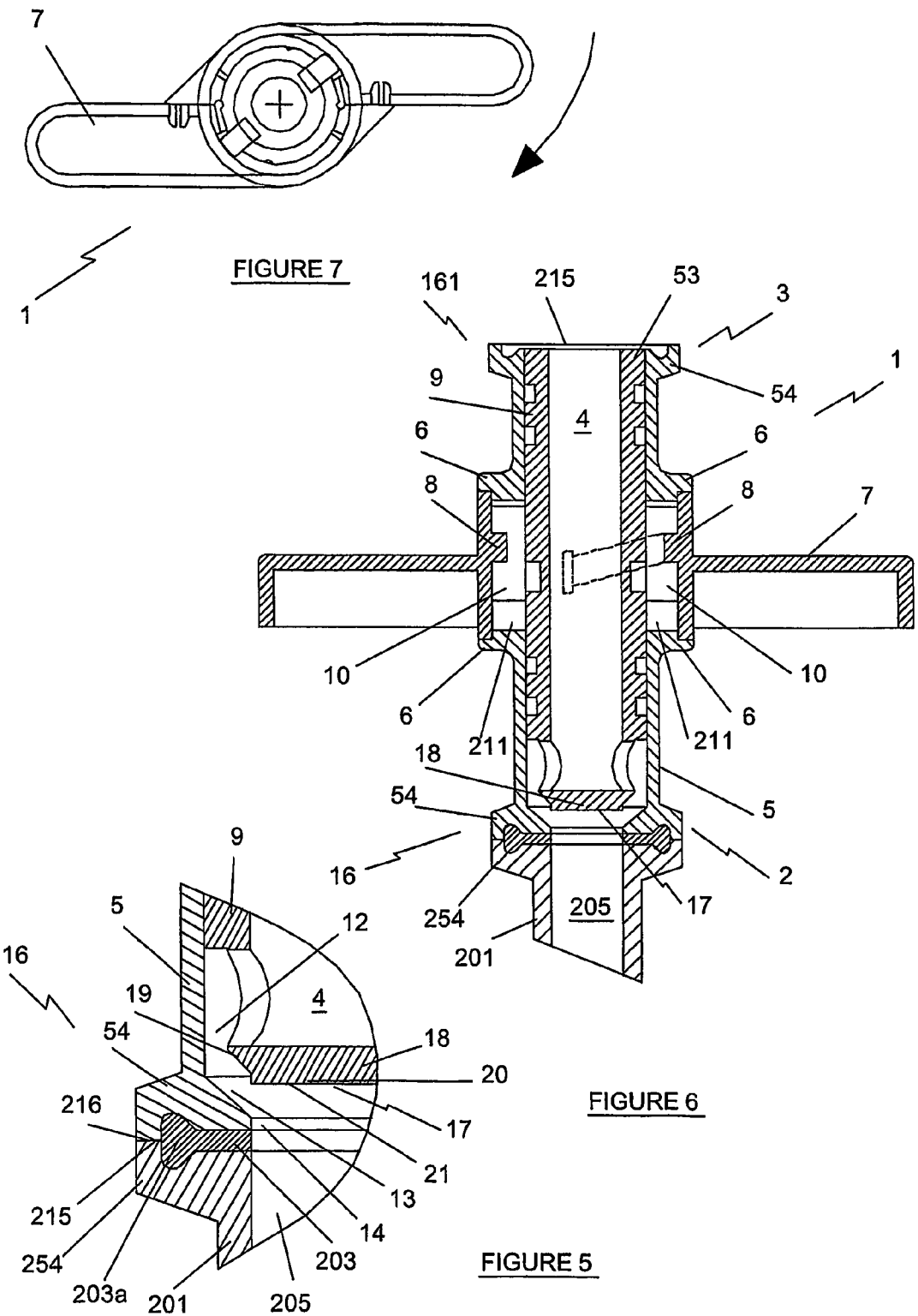

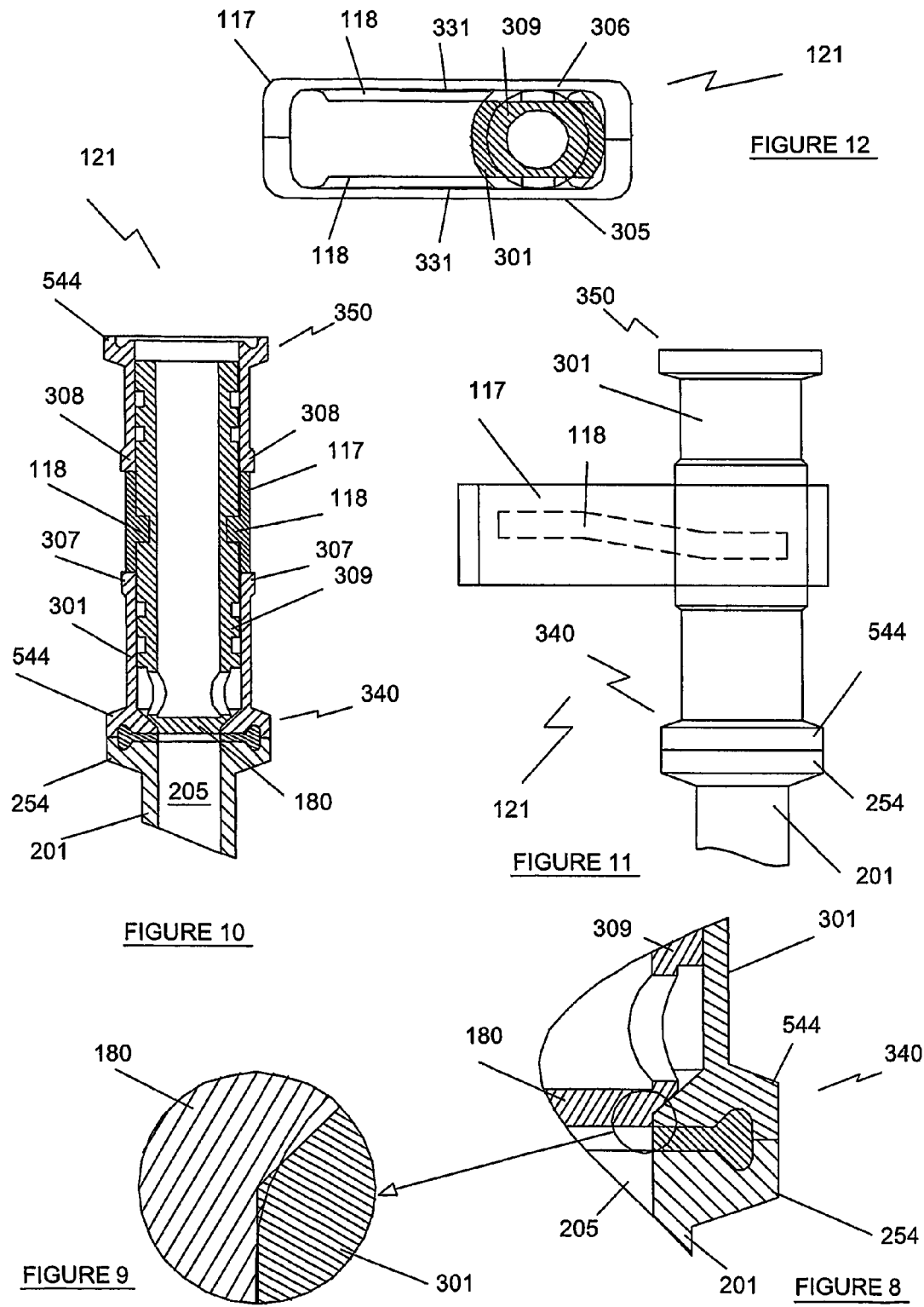

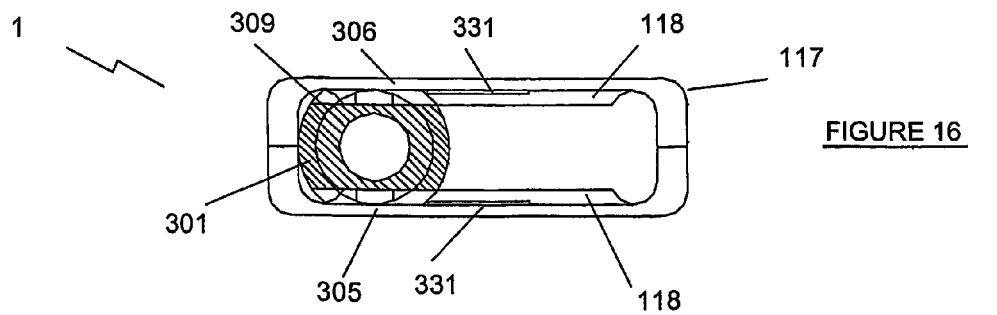
FIGURE 16
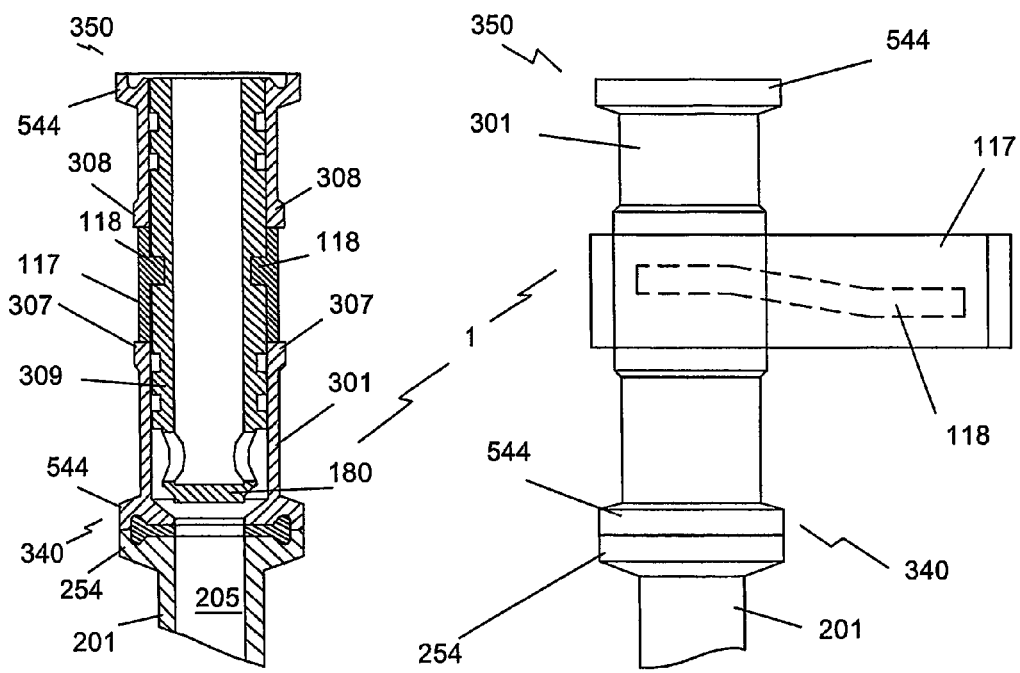
FIGURE 14
FIGURE 15
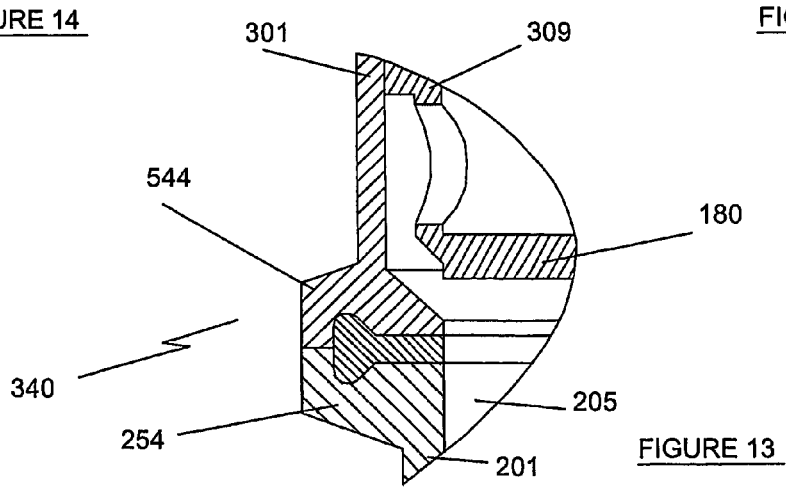
FIGURE 13

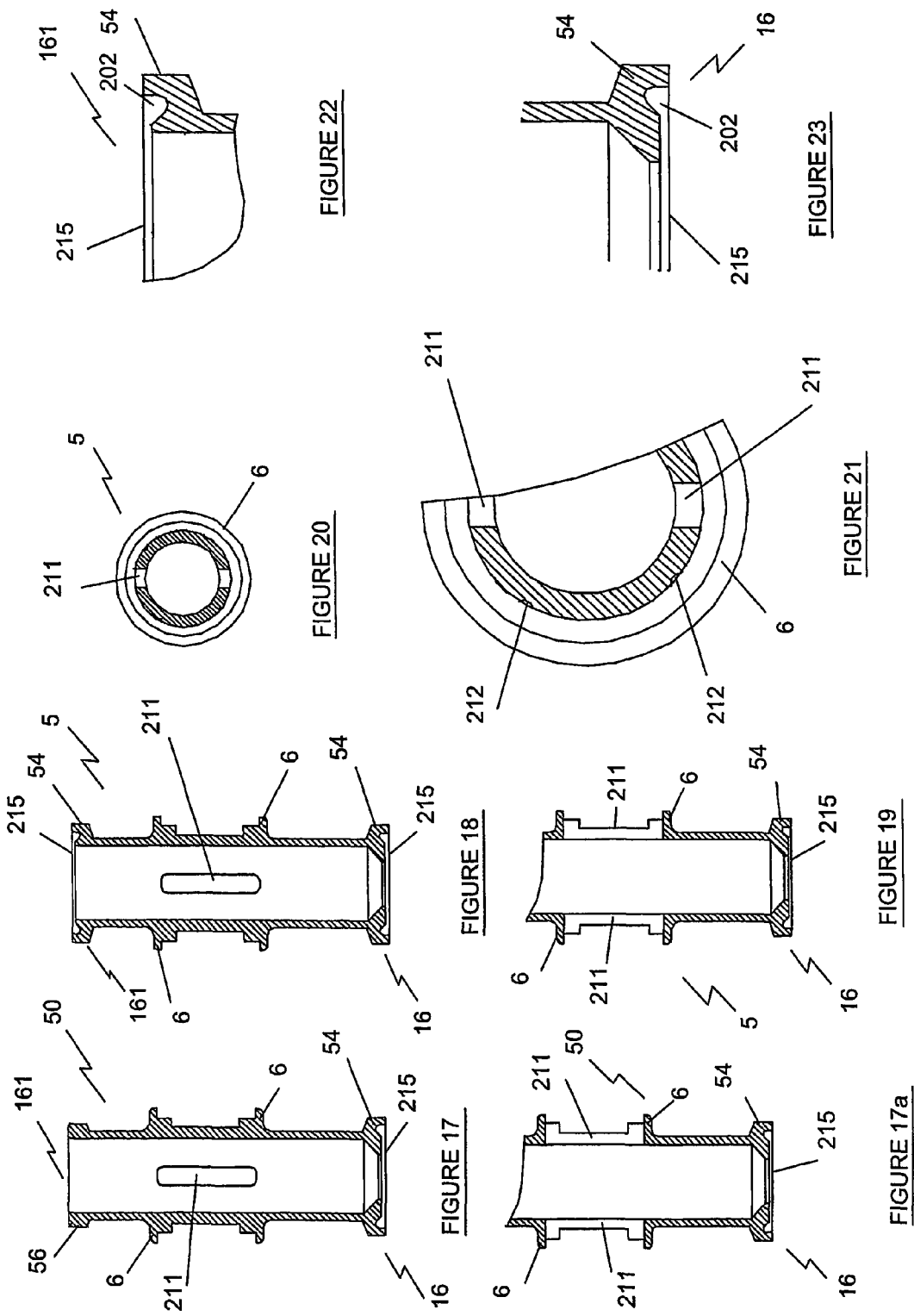

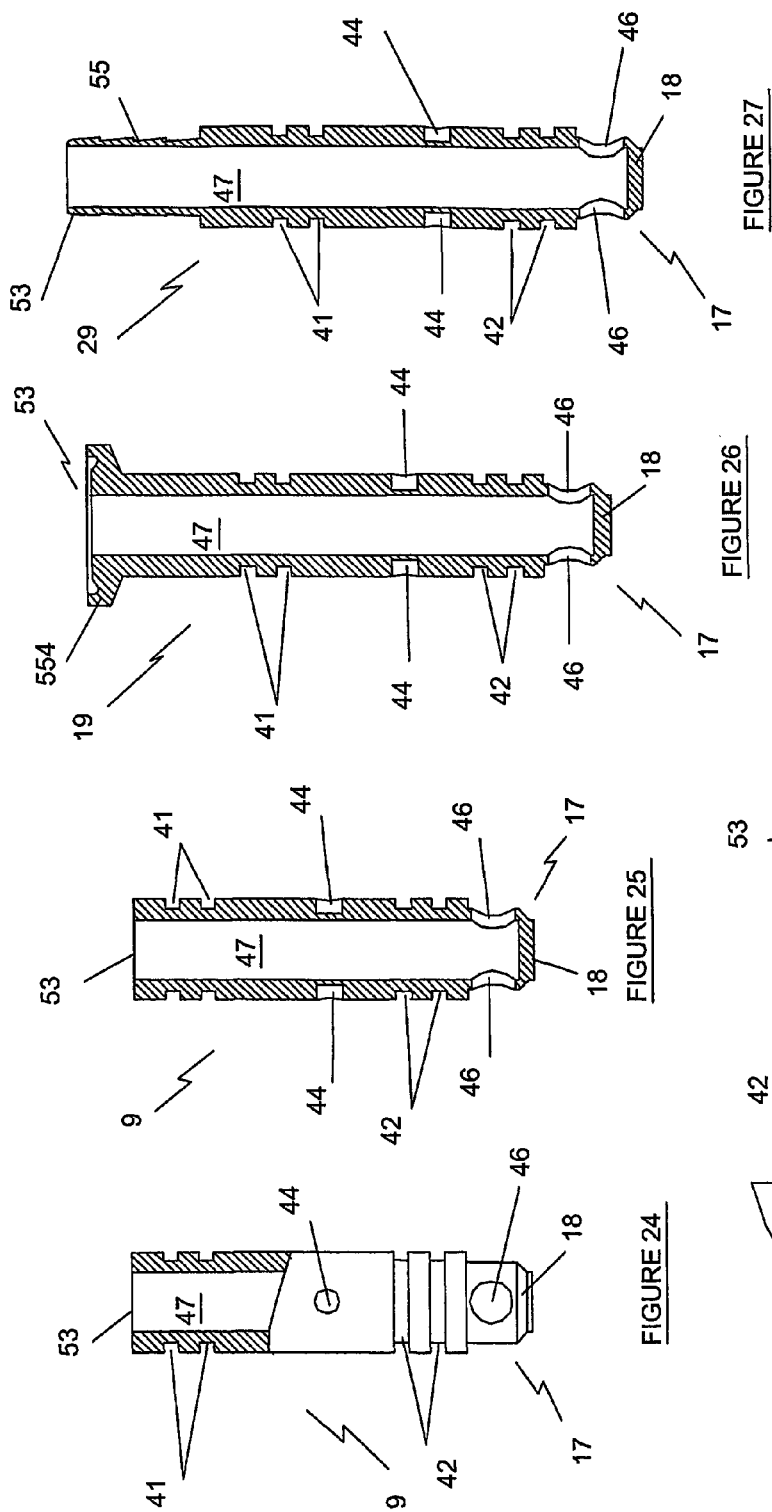

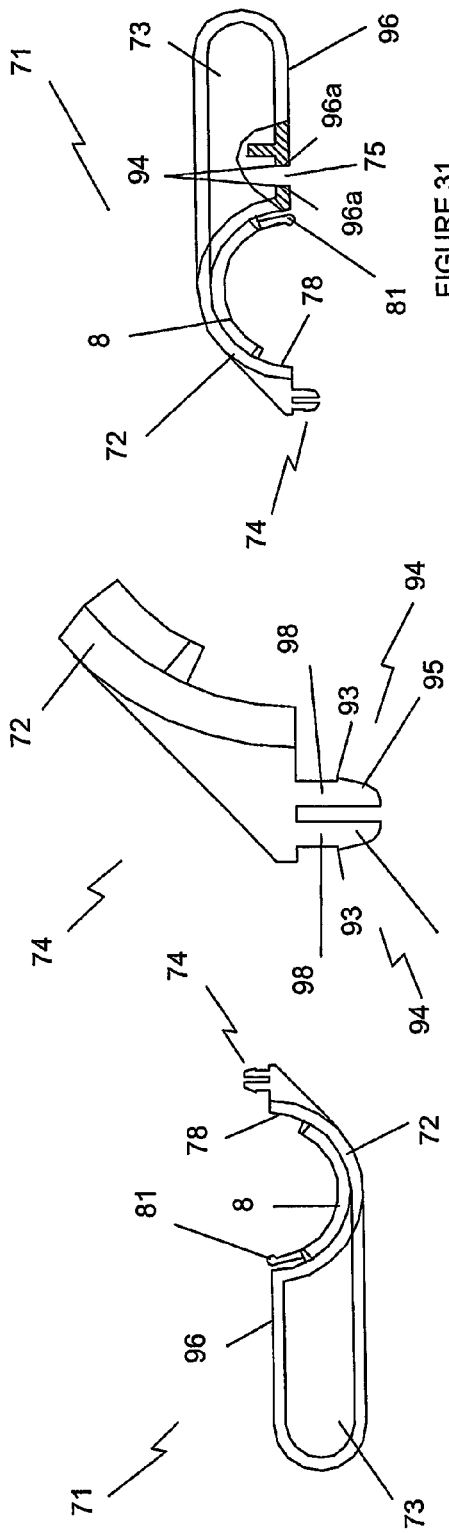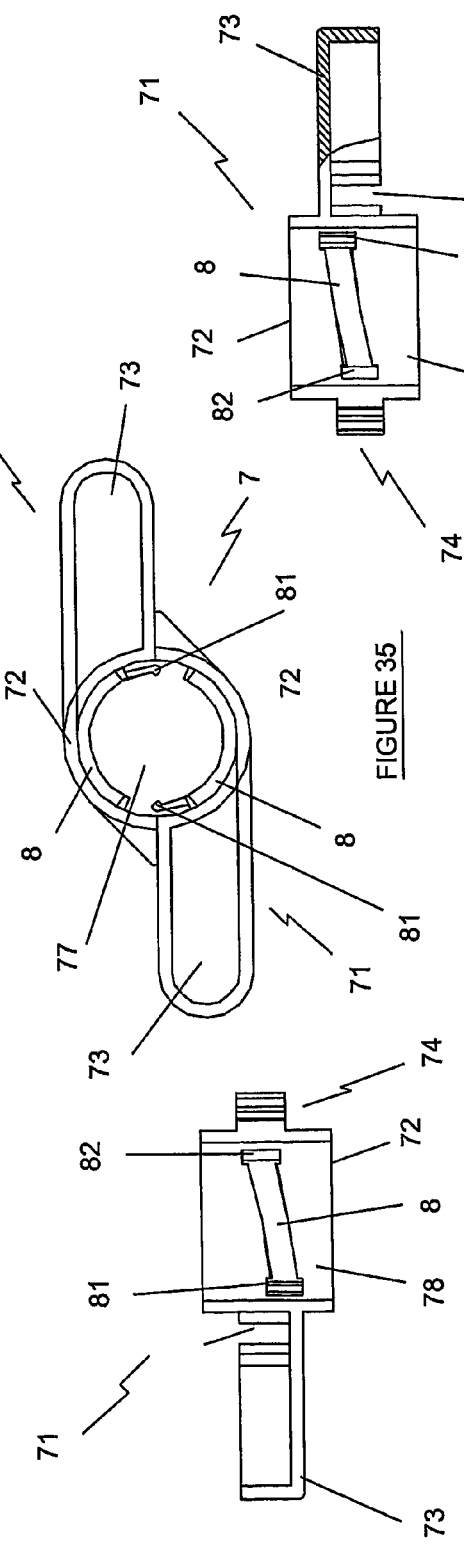

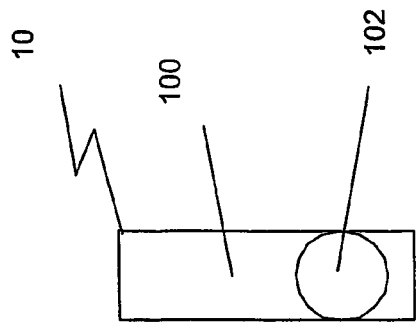
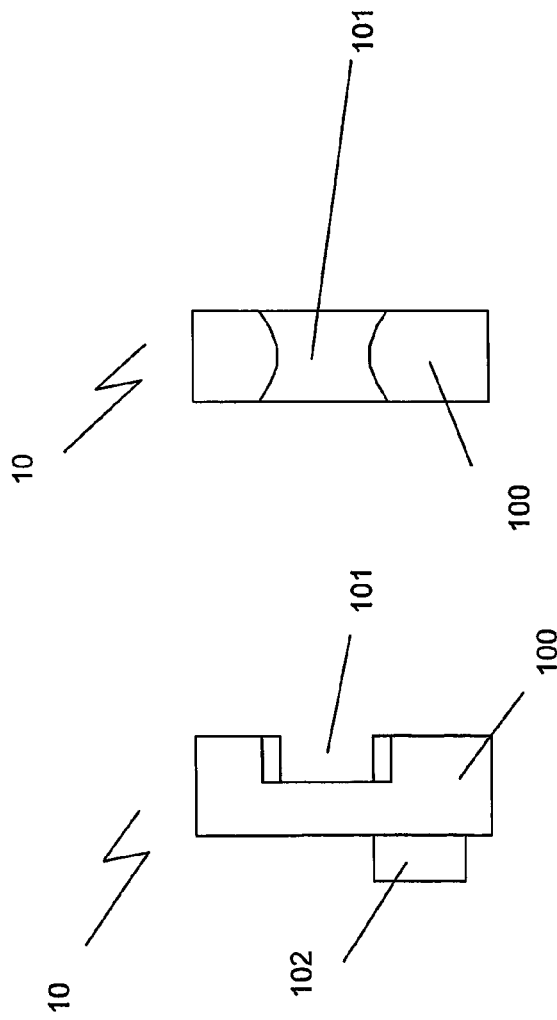
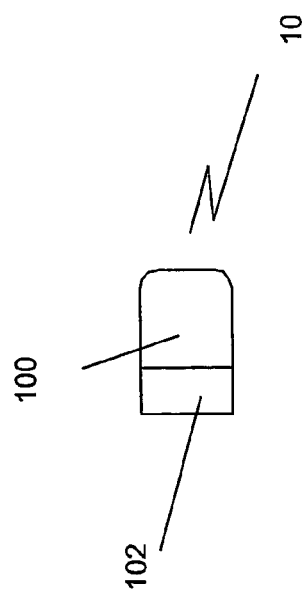

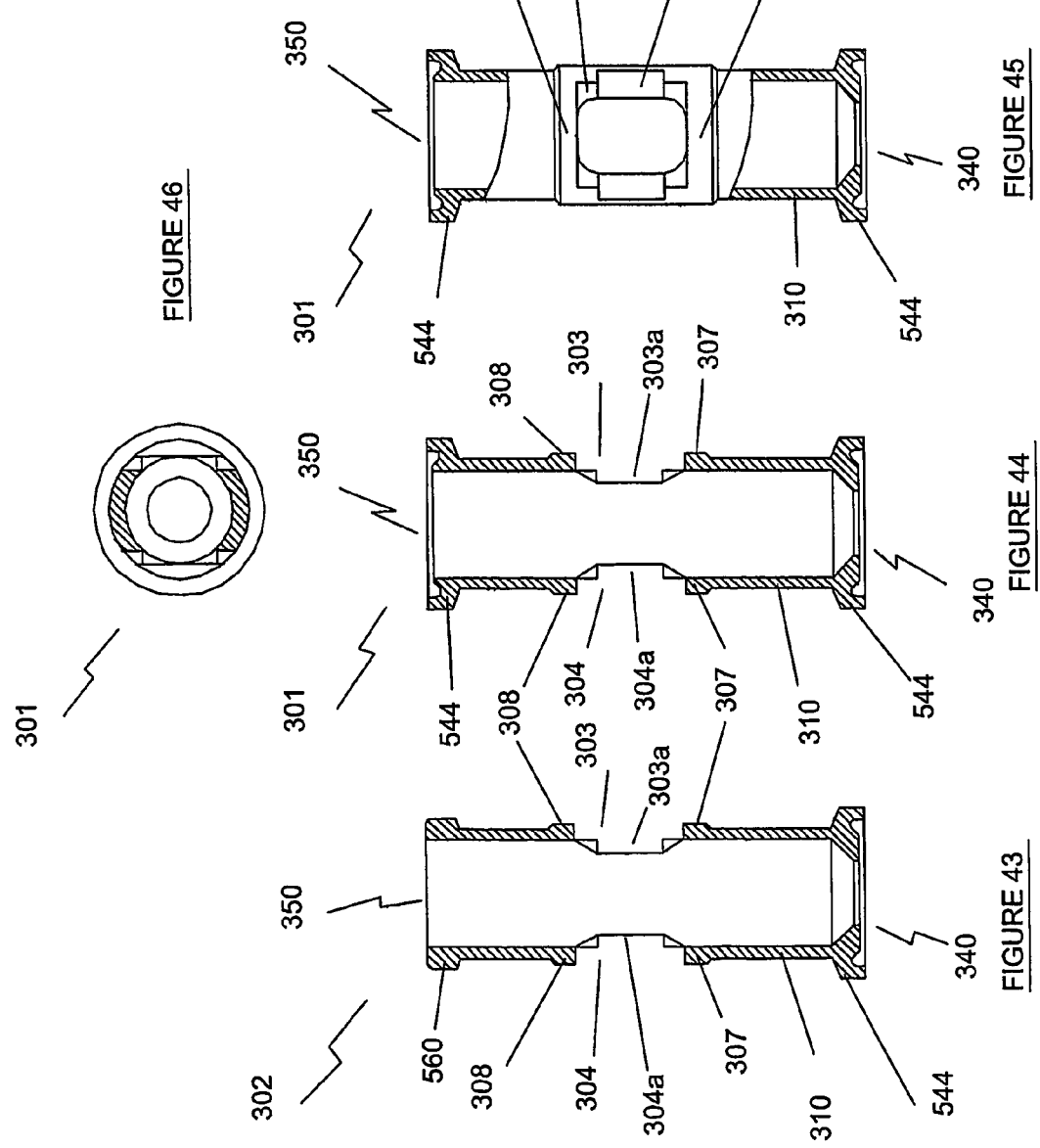

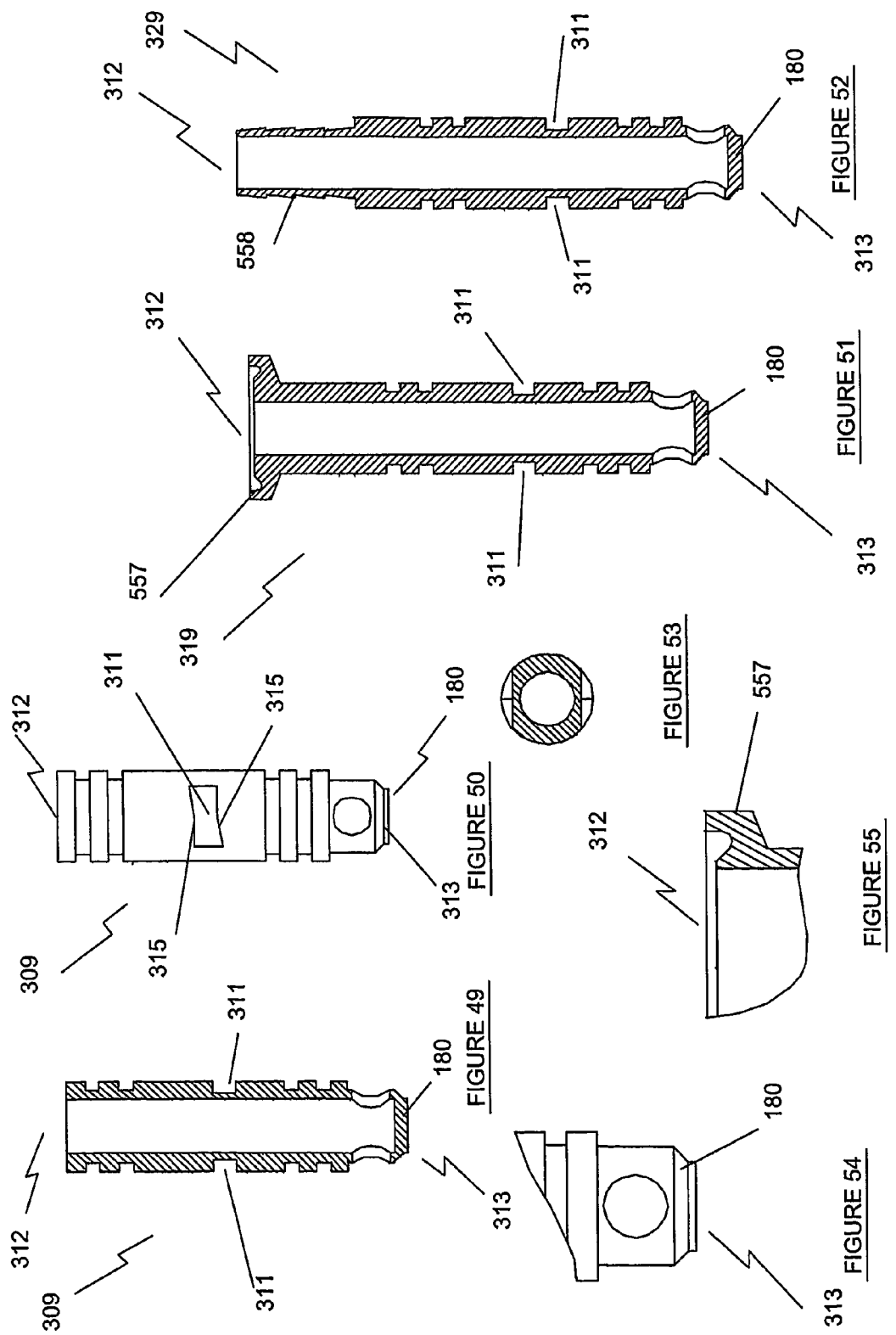

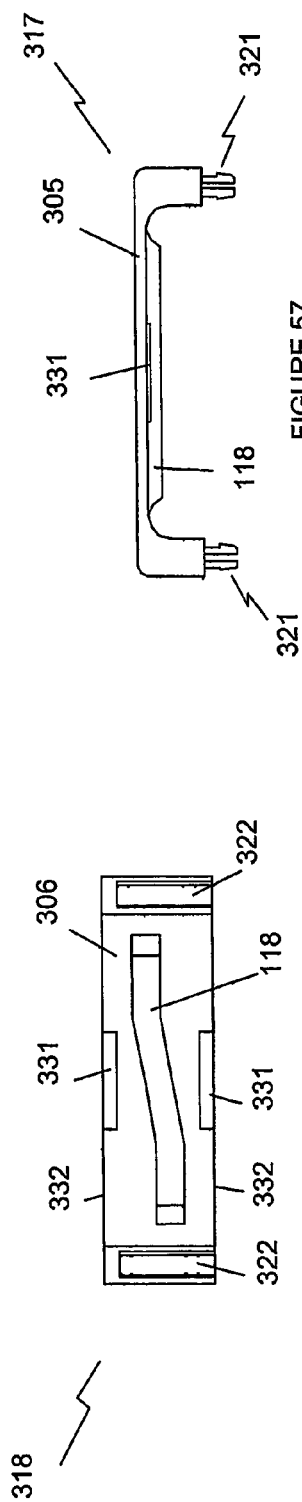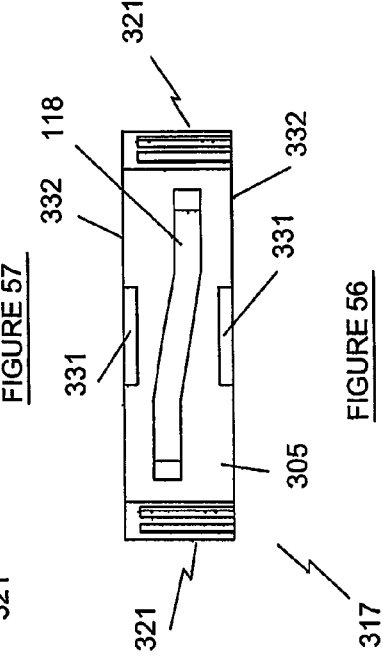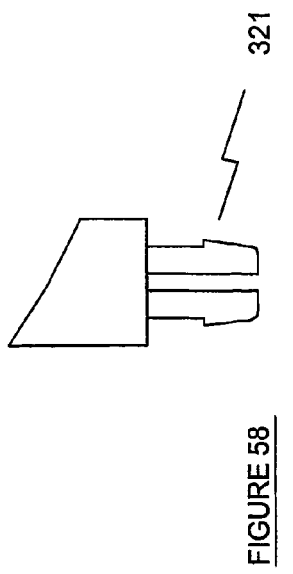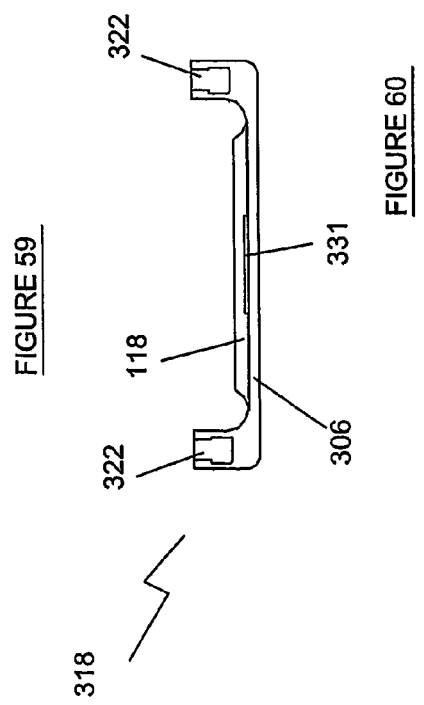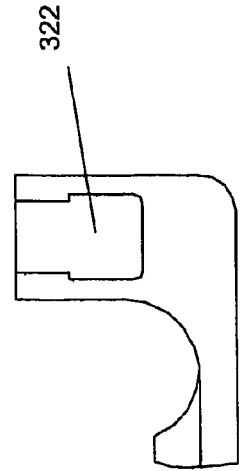

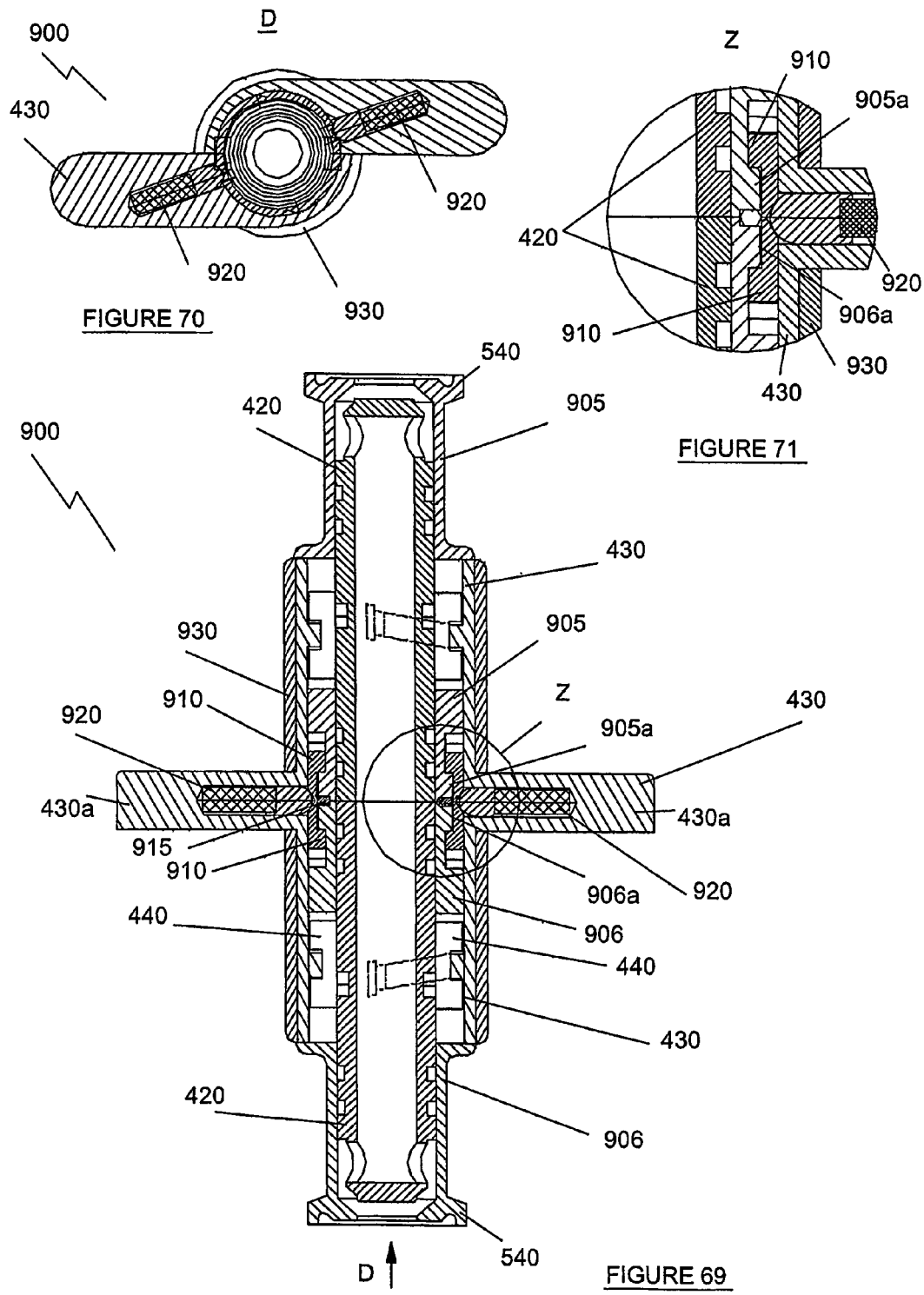

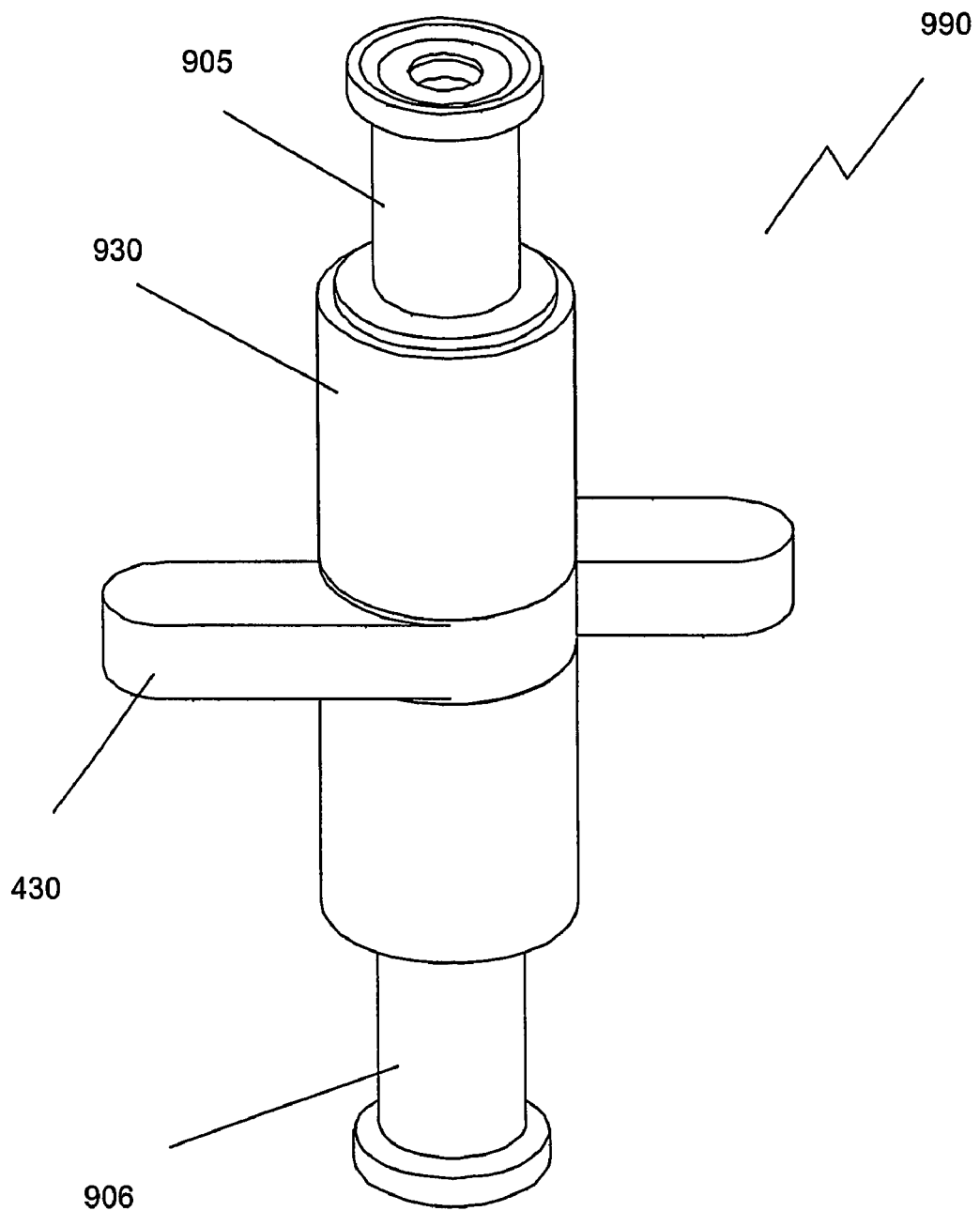
FIGFURE 74

VALVE

CROSS-REFERENCE TO RELATED APPLICATIONS

This application is the National Stage of International Application No. PCT/US2004/024732, filed Jul. 30, 2004, which claims the benefit of U.S. Provisional Application No. 60/491,737, filed Aug. 1, 2003, the contents of which is incorporated by reference herein.

FIELD OF THE INVENTION

The present invention relates to a valve apparatus and in particular to a valve apparatus useful in systems for the sterile transfer of fluids.

BACKGROUND OF THE INVENTION

Validation and accountability are vital in most scientific industries and especially so in the pharmaceutical and biotechnological industries. A major challenge to these industries is the need to demonstrate accurately and reproducibly that sterility is achieved and maintained throughout production lines within a plant. This must be done in a manner which meets the stringent requirements of regulatory bodies such as the United States FDA. Acceptable standards can be difficult to be met when a substance is transferred from one sterile location to another sterile location by non direct means.

One current practice includes providing a holding vessel into which substance can be transferred by means of a connecting valve. The holding vessel is transferred to the second sterile location and the substance is then transferred from the holding vessel into the second sterile location via one or more connecting valves. The connecting valves and holding vessel can be sterilised using conventional techniques such as gas, radiation or steam sterilisation. However during connection of the connecting valve to the first sterile location, the external connecting surface of the connecting valve is exposed to the atmosphere and sterility of the valve is compromised.

Alternative methods of substance transfer suffer from similar problems.

For example, in the use of an autoclavable port, where a non-sterile male port is attached to an empty non-sterile bulk vessel prior to sterilization, the entire assembled apparatus is then sterilised by autoclaving. However, a major disadvantage of this technique is that the vessel must be empty before sterilisation.

Alternatively, an irradiated port can be used, where a non-sterile male port is attached to an empty non-sterile disposable bag prior to sterilisation of the whole by irradiation. Again a major disadvantage associated with this system is that the bag must be empty before sterilisation.

A further method of substance transfer involves connecting a transfer port to a vessel under aseptic conditions. With this method it is irrelevant whether or not the vessel is empty or filled. However despite the necessity to undertake these actions in a designated 'Grade A' zone, there is an increased risk of contamination due to the making and breaking of various connections. The mere fact that a 'Grade A' zone is required to complete these actions requires a significant financial investment by a company wishing to employ this technique.

Another technique incorporates the use of a tube fuser. A sterile bulk vessel is attached to tubing emanating from a sterile port through a tube fuser. This technique is undesirable for numerous reasons including the restricted choice of tubing. This in turn limits the types of substance that can be transferred through the tubing. It is also undesirable to use wetted tubing. Furthermore there is also a potential risk of cross-contamination and re-contamination.

Despite the numerous attempts to find a sterile method of substance transfer none have been wholly successful. In all of the above techniques the sterility of the port or valve used to transfer the substance from one vessel to another is compromised during the connection process or is susceptible to contamination. This is undesirable and leads to problems when validating a product.

Piston-operated valves for the above applications are known. These act by moving a piston up and down or sliding over and back within an apertured housing so as to cover or uncover the fluid communication apertures of the housing. O-ring seals are provided for sealing between the open and closed valve positions. Such valves therefore have slots for receiving the O-rings and the difficulties of assuring that these slots and the spaces about them are not subject to contamination render them questionable for use in sterile transfer systems.

WO 03/090842 discloses a valve including a piston moveable within a housing. The opening of the valve including a sealing plug member connected to the piston so that as the piston is withdrawn away from the opening, it pulls the plug with it, causing the plug to rupture about a weakening formed in its rim and to tear away from the opening thereby breaking the seal.

It is an object of the present invention to seek to alleviate the aforementioned problems.

SUMMARY OF THE INVENTION

Accordingly, the invention provides a valve comprising a body having first and second open ends and a passageway for fluid between the ends, the first end including a first coupling means for sealingly connecting the body about an opening of a first external device and a seal blocking an open area of the first end which in use is placeable in register with the opening of the external device, the valve further including a seal displacement means movable within the body so as to interrupt the seal permitting fluid to pass along the passageway between the ends, the coupling means and the seal presenting a sterilisable mating surface for sealingly mating with a mating surface about the opening in the first external device, wherein the seal is formed between a first plastics portion movable by the seal displacement means and a second plastics portion disposed about the open area of the first end of the valve.

Ideally, one of the plastic portions has a protruding sharp rim and the other plastics portion of the seal has a curved surface area so that when the valve is in the closed position, the sharp rim engages the curved surface area and displaces a portion of the curved surface area thereby elastically deforming the materials of the sharp rim and the curved surface area to seal the opening of the valve.

Preferably, the body of the valve is manufactured from a plastic material.

Advantageously, the engagement of the sharp rim with the curved surface area occurs during a linear motion of the sharp rim relative to the curved surface area Ideally, the first plastic portion is integrally formed with the seal displacement means.

Preferably, the first plastic portion is provided by a plastic plug integrally formed with the seal displacement means.

Ideally, the second plastic portion is integrally formed with the body of the valve.

Optionally, the body of the valve is manufactured from a non plastic material.

Ideally, the second plastic portion comprises a wall defining a bore portion having a cross-section converging towards the first end of the valve which in turn leads to a wall defining a bore portion having a substantially uniform cross-section which is located adjacent the first end of the valve, the boundary between the wall defining the converging bore portion and the wall defining the uniform bore portion defining the sharp rim, the first plastic portion having a body portion with a cross-section converging towards the first end of the valve and leading to an end portion with a uniform cross-section, the end portion being adjacent the first end of the valve in use and a transitional surface between the external surface of the body portion and the external surface of the end portion of the first plastic portion defining the curved surface area so that when the opening of the valve is sealed the sharp rim engages the curved surface area and displaces a portion of the curved surface area thereby elastically deforming the materials of the sharp rim and the curved surface portion.

Preferably, the curved surface area has a predetermined radius.

In a preferred embodiment, the second end of the body comprises a second coupling means with a mating surface for sealingly connecting the body about an opening of a second external device. Most conveniently, the distance between the mating surfaces of the first and the second coupling means remains unchanged during movement of the seal displacement means within the body between open and closed positions of the valve so that in use the valve can connect mating surfaces about openings of a first and a second external devices separated by a distance equal to the distance between the mating surfaces of the body.

In another embodiment, the seal displacement means travels at least partially outside of the second end of the body on actuation of the valve and the displacement means comprise first and second ends, the first end comprising the first plastic portion and the second end comprising a coupling means for sealingly connecting the displacement means about an opening of a second external device.

Advantageously, the valve has means for displaying to a user the actuation state of the valve.

In a preferred embodiment, the body comprises a hollow housing extending between the first and the second open ends and the seal displacement means comprises a piston slidably movable within the housing, the piston having the first plastic portion formed at one end thereof.

Conveniently, the valve comprises an operating means for actuating the valve.

Most preferably, the operating means comprises an actuator externally mounted on the body and movable between a first and a second end position, the actuator being linked with the seal displacement means so that movement of the actuator between the first and the second end positions causes the seal displacement means to translate along the passageway between open and closed positions.

Ideally, the actuator is linked with the seal displacement means via a cam pair.

Most preferably, at least one guide element is provided in the valve to prevent rotational motion of the seal displacement means and to permit the seal displacement means to move only linearly in the passageway.

In yet another embodiment, a seal is provided at both the first and the second open ends of the body, each seal having a seal displacement means movably disposed within the passageway of the body so that the first and/or second ends may be sealed or opened.

In another aspect, the invention provides a valve comprising a body having first and second open ends and a passageway for fluid between the ends, the first end including a coupling means for sealingly connecting the body about an opening of an external device and a seal blocking the open area of the first end which in use is placeable in register with the opening of the external device, the valve further including a cam and follower arrangement for moving a seal displacement means movable within the body comprising an actuator, positioned concentrically about said body and rotatable about the axis of said body and having a pair of shaped slots and a piston having a pair of opposing outwardly projecting pins wherein each of said outwardly projecting pins are cooperatively engaged within said shaped slots and wherein each of said shaped slots has a first section that is substantially parallel to the longitudinal axis of said piston and a second section that is curved in a direction substantially perpendicular to the longitudinal axis of said piston, the piston is provided with a first plastics sealing plug movable by the seal displacement means into sealing engagement with a second plastics portion disposed about the open area of the first end.

Preferably, said first section contacts said pins from 0 to 56 degrees rotation of said actuator and said second section contacts said pins from 56 to 80 degrees rotation of said actuator.

Ideally, said seal displacement means is movable between a ready state in which said first and second plastics portions are in sealing contact and the valve is closed and a deployed state in which said first plastics portion is displaced from contact with said second plastics portion and moved with the seal displacement means away from the mating surface so that the valve is open.

Advantageously, the seal displacement means and said sealing plug are withdrawn into said coupling means as the seal displacement means moves from the ready state to the deployed state.

Ideally, the actuator includes a safety lock means for preventing undesired movement of the seal displacement means.

Advantageously, the valve includes visible or tactile indication means for indicating to a user the position of the valve between its ready and deployed states.

Most preferably, the seal displacement means includes a first and a second internal seal arranged concentrically between said body and said seal displacement means, and longitudinally between said first and second open ends, wherein said first and second seal are separated by a distance parallel to the longitudinal axis of said displacement means.

Ideally, the distance separating said first and second seal is less than the distance the seal displacement means moves from the ready state to the deployed state.

Most preferably, the piston moves non-rotationally relative to the housing to open or close the valve.

In yet another aspect, the invention provides a valve comprising a body having first and second open ends and a passageway for fluid between the ends, the first end including a first coupling means with a first mating surface and the second end including a second coupling means with a second mating surface, the first and the second coupling means being sealingly mateable with mating surfaces about openings of first and second external devices respectively and a seal blocking an open area of the first end which in use is placeable in register with the opening of the first external device, the valve further including a seal displacement means movable within the body so as to interrupt the seal permitting fluid to pass along the passageway between the ends, the first mating surface and the seal presenting a sterilisable surface, wherein the distance between the first and the second mating surfaces of the valve remains unchanged during movements of the seal displacement means within the body.

Ideally, the body comprises a hollow housing extending between the first and the second open ends and the seal displacement means comprises a piston slidably movable within the housing.

Advantageously, the valve includes an operating means for actuating the valve.

Most preferably, the operating means comprises an actuator externally mounted on the body and movable between a first and a second end position, the actuator being linked with the seal displacement means so that movement of the actuator between the first and the second end positions causes the seal displacement means to translate along the passageway between open and closed positions and the actuator is linked with the seal displacement means via a cam pair.

Ideally, at least one guide element is provided in the valve to prevent rotational motion of the seal displacement means and to permit the seal displacement means to move only linearly in the passageway.

Conveniently, the valve includes means for displaying to a user the actuation state of the valve.

Optionally, a seal is provided at both the first and the second open ends of the body, each seal having a seal displacement means movably disposed within the passageway of the body so that the first and/or second ends may be sealed or opened.

In a further aspect, the invention provides, a valve comprising a body having first and second open ends and a passageway for fluid between the ends, the first end including a first coupling means with a first mating surface and the second end including a second coupling means with a second mating surface, the first and the second coupling means being sealingly mateable with mating surfaces about openings of a first and a second external devices, in which first and second seals are provided for removably blocking open areas of the first and the second ends, respectively, which in use are placeable in register with the openings of the first and the second external devices, the valve further including a pair of seal displacement means movable within the body so as to interrupt at least one of the seals permitting fluid to pass along the passageway between the ends, the first mating surface and the first seal presenting a first sterilisable surface, and the second mating surface and the second seal presenting a second sterilisable surface.

Preferably, the body comprises a hollow housing extending between the first and the second open ends and the seal displacement means comprises a piston slidably movable within the housing.

Conveniently, the valve includes an operating means for actuating the valve.

Most preferably, the operating means comprises at least one actuator externally mounted on the body and movable between a first and a second end position, the actuator being linked with at least one of the seal displacement means so that movement of the actuator between the first and the second end positions causes the seal displacement means to translate along the passageway between open and closed positions and the actuator is linked with the seal displacement means via a cam pair.

Ideally, at least one guide element is provided in the valve to prevent rotational motion of the seal displacement means and to permit the seal displacement means to move only linearly in the passageway.

Conveniently, the valve includes means for displaying to a user the actuation state of the valve.

Optionally, the distance between the first and the second mating surfaces of the valve remains unchanged during movements of the seal displacement means within the body.

The valve according to the invention may be a single use valve. Alternatively and even more preferably, it may be a multiple use valve and in particular, it may be repeatedly opened and shut in situ in the line in which it is incorporated. This enables the valve to facilitate the operation of those processes in which sampling of product passing through the line is desirable from time to time.

In the most advantageous arrangement of the invention, the action of opening and closing the valve is effected by linearly displacing a piston axially within a housing so as to form or interrupt a seal. Most ideally, any rotational movement of the seal is avoided.

BRIEF DESCRIPTION OF THE DRAWINGS

The invention will now be described with reference to the accompanying drawings which show by way of example only, seven embodiments of a valve in accordance with the invention. In the drawings:

FIG. 1 is a detail view of a seal of a first embodiment of a valve in a closed position;

FIG. 2 is a magnified detail view of the seal of FIG. 1;

FIG. 3 is a sectional elevation of the first embodiment of the valve in the closed position;

FIG. 4 is a bottom view of FIG. 3 in the direction of arrow A of FIG. 3;

FIG. 5 is a detail view of the seal of the first embodiment of the valve in an open position;

FIG. 6 is a sectional elevation of the first embodiment of the valve in the open position;

FIG. 7 is a bottom view of FIG. 6 in the direction of arrow B of FIG. 6;

FIG. 8 is a detail view of a seal of a third embodiment of the valve in a closed position;

FIG. 9 is a magnified detail view of the seal of FIG. 8;

FIG. 10 is a sectional elevation of the third embodiment of valve in the closed position;

FIG. 11 is an elevation of the third embodiment of the valve in the closed position;

FIG. 12 is a plan view of FIG. 11;

FIG. 13 is a detail view of the seal of the third embodiment of the valve in an open position;

FIG. 14 is a sectional elevation of the third embodiment of the valve in the open position;

FIG. 15 is an elevation of the third embodiment of the valve in the open position;

FIG. 16 is a plan view of FIG. 15;

FIG. 17 is a front sectional elevation of a housing for the second embodiment of the valve;

FIG. 17a is a side sectional elevation of the housing of FIG. 17;

FIG. 18 is a front sectional elevation of a housing for the first embodiment of the valve;

FIG. 19 is a side sectional elevation of the housing of FIG. 18;

FIG. 20 is a sectional plan view of FIG. 17;

FIG. 21 is an enlarged partial view of FIG. 20;

FIG. 22 is a detail view of a flange at a second end of the housing of FIG. 18;

FIG. 23 is a detail view of a flange of a first end of the housing of FIG. 18;

FIG. 24 is a partially sectional front elevation of a piston for the first embodiment of the valve;

FIG. 25 is a side sectional elevation of the piston of FIG. 24;

FIG. 26 is a side sectional elevation of a piston for the second embodiment of the valve;

FIG. 27 is a side sectional elevation of another piston for the third embodiment of the valve;

FIG. 28 is an enlarged partial view of FIG. 24;

FIG. 29 is an enlarged partial view of FIG. 26;

FIGS. 30 and 31 are front and plan views respectively of one component half of a rotary actuator for the first and the second embodiments of the valve;

FIG. 32 is an enlarged partial view of FIG. 31;

FIGS. 33 and 34 are front and bottom views respectively of the other component half of the rotary actuator for the first and the second embodiments of the valve;

FIG. 35 is a plan view of the assembled rotary actuator for the first and the second embodiments of the valve;

FIGS. 36, 37, 38 and 39 are front, first side, second side and plan views respectively of a cam follower for the first and the second embodiments of the valve;

FIG. 43 is a sectional elevation of a housing for a fourth embodiment of the valve;

FIG. 44 is a sectional elevation of a housing for the third embodiment of the valve;

FIG. 45 is a partially sectional side elevation of the housing of FIG. 44;

FIG. 46 is a sectional plan view of FIG. 44;

FIG. 47 is a detail view of a flange at a second end of the housing of FIG. 45;

FIG. 48 is a detail view of a flange of a first end of the housing of FIG. 45;

FIG. 49 is a sectional elevation of a piston for the third embodiment of the valve;

FIG. 50 is a side elevation of the piston of FIG. 49;

FIG. 51 is a sectional elevation of a piston for the fourth embodiment of the valve;

FIG. 52 is a sectional elevation of another piston for the fourth embodiment of the valve;

FIG. 53 is a plan sectional view of the piston of FIG. 50;

FIG. 54 is an enlarged partial view of FIG. 50;

FIG. 55 is a detail view of a flange of a second end of the piston of FIG. 51;

FIGS. 56 and 57 are front and plan views respectively of one component half of a sliding actuator for the third and the fourth embodiments of the valve;

FIG. 58 is an enlarged partial view of FIG. 57;

FIGS. 59 and 60 are front and bottom views respectively of the other component half of the sliding actuator for the third and the fourth embodiments of the valve FIG. 61 is an enlarged partial view of FIG. 60;

FIG. 69 is a sectional elevation of a sixth embodiment of the valve in an open position;

FIG. 70 is a bottom view of the valve of FIG. 69 in the direction of arrow D;

FIG. 71 is an enlarged view of area Z of the valve of FIG. 69;

FIG. 74 is a perspective view of the valve of FIG. 72;

DETAILED DESCRIPTION

Figure 40:
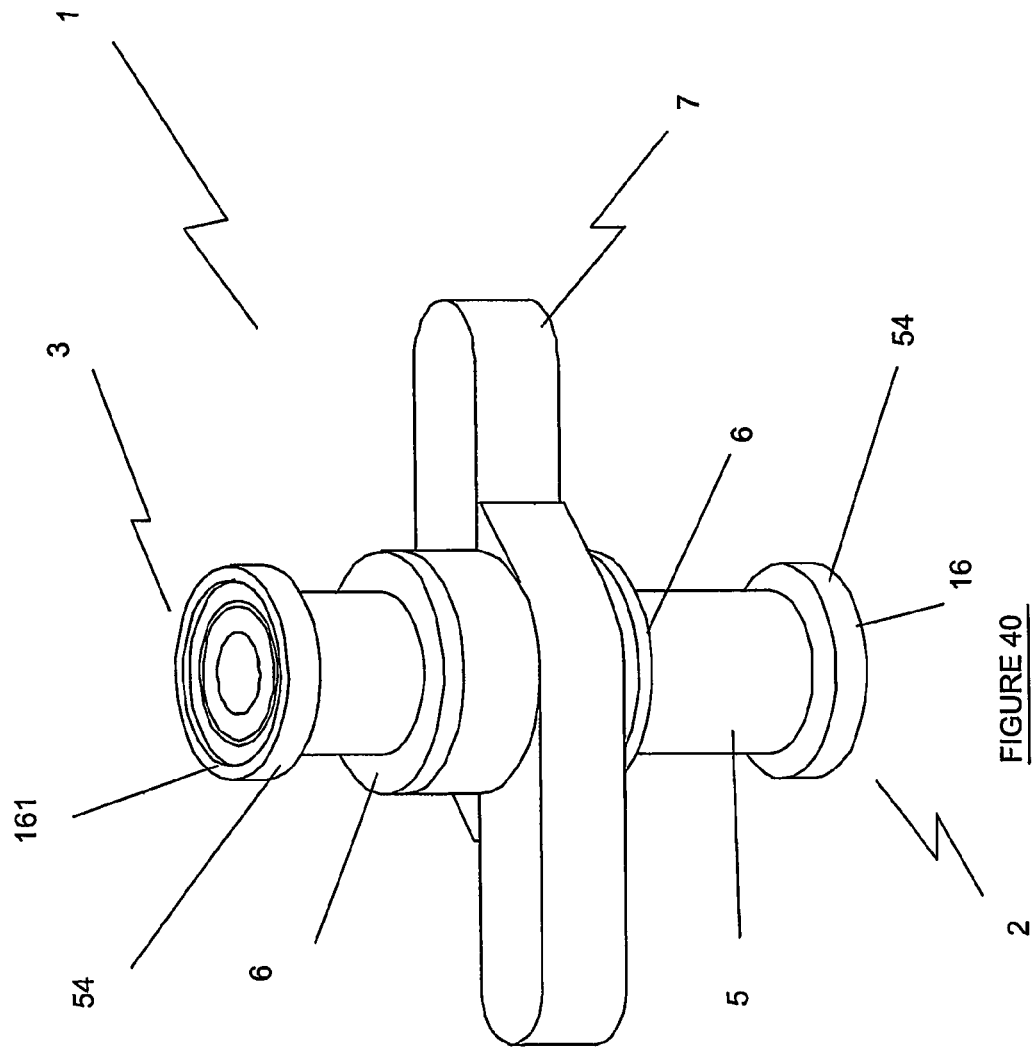
FIG. 40 is a perspective view of a first embodiment of the valve of the invention.

Referring to the drawings and initially to FIGS. 1 to 7 there is shown a first embodiment of the valve according to the invention indicated generally by the reference numeral 1. The valve 1 has a body having first and second open ends 2, 3 and a passageway 4 extending between the ends 2, 3.

The body of the valve 1 comprises a hollow tubular housing 5 and an actuator 7 rotatably mounted on the housing 5. The housing 5 has a first end 16 and a second end 161 and an internal bore formed therebetween. The first end 16 and the second end 161 in use are located at the first end 2 and the second end 3 of the valve respectively. The actuator 7 has a pair of cams 8 on the inner surface of actuator 7. A piston 9 is disposed within the housing 5 and a cam follower 10 is mounted between the piston 9 and each cam 8 and extends through one of a pair of opposing through-slots 211 extending parallel to the longitudinal axis of the housing 5. The cam followers 10 are engaged with both the cams 8 and the piston 9 so that rotation of the actuator 7 causes the cams 8 to co-operate with the cam followers to enable translation of the piston 9 along the longitudinal axis of the housing 5. The through-slots 211 prevent the piston 9 from rotating within the housing 5.

The internal bore of the housing 5 comprises a first bore portion 12 adjacent the first end 16 of the housing which has a substantially uniform cross-section leading in a direction towards the first end 2 of the valve 1 to a second bore portion 13 having a cross-section converging towards the end 2 which in turn leads to a third bore portion 14 having a substantially uniform cross-section. The third bore portion 14 is located adjacent the first open end 2 of the valve 1. The boundary between the inner surface of the housing 5 defining the bore portion 13 and the inner surface of the housing 5 defining the bore portion 14 defines a sharp rim 15.

The piston 9 has a first end 17 and a second end 53 and an internal bore 47 extending between the ends. The first end 17 of the piston 9 which in use is located adjacent the first open end 2 of the valve comprises a plug 18. The plug 18 has a body portion 11 with a cross-section converging towards the first end 17 of the piston 9 and leading to an end portion 20 with a uniform cross-section. The end portion 20 is adjacent the first open end 2 of the valve 1 in use. The end portion 20 comprises an end surface 21. A transitional surface between the body portion 11 and the end portion 20 of the plug 18 defines a curved surface area 22 having optionally a predetermined radius.

The plug 18 is shown formed integrally with the piston 9, but of course the invention is not in any way restricted to such a formation and many other means of connecting the plug 18 and the piston 9 are possible.

Transition between open and closed states of the valve 1 is performed by rotating the actuator 7 to displace the piston 9 and plug 18 by a linear movement which is parallel to the longitudinal axis of the housing 5.

When the actuator 7 is rotated clockwise, as best seen in FIGS. 6 and 7, the cams 8 co-operate with the cam followers 10 causing the cam followers to travel along the through-slots 211, so as to cause the piston 9 together with the plug 18 to move axially towards the first end 16 of the housing 5. During the axial travel of the piston 9 the sharp rim 15 engages the curved surface area 22 of the plug 18 and displaces a portion of the curved surface area 22 of the plug 18 elastically deforming the plastic materials of the sharp rim 15 and the curved surface area 22 (see FIG. 2) thus bringing the valve 1 into a closed state as shown in FIGS. 3 and 4. In the closed state of the valve 1 the plug 18 seals the opening of the first end 16 of the housing 5 so that the end portion 20 of the plug 18 occupies the third bore portion 14 of the housing 5 whilst the body portion 11 of the plug 18 occupies the second bore portion 13 of the housing 5.

When the actuator 7 is rotated anticlockwise, as shown in FIG. 4, the cam followers 10 travel in the reverse direction along the through-slots 211 causing the piston 9 together with the plug 18 to move away from the first end 16 of the housing 5. The sharp rim 15 disengages from the curved surface area 22 of the plug 18 thus opening the valve 1 for passage of fluid. The plastics materials of the curved surface area 22 and the sharp rim 15 may remain partially deformed after opening of the valve, but this deformation does not affect the integrity of a seal formed during a second and subsequent actuations of the valve.

The valve 1 is a fixed length valve which is used when it is necessary to connect openings of vessels or pipes which are positioned at a fixed distance from each other. The travel of the piston 9 occurs within the housing 5, so that no part of the piston 9 extends outside the housing 5.

It will be appreciated that the actuator 7, the cams 8, the housing 5, and the cam followers 10 can be mutually arranged so that the valve is opened by rotating the actuator 7 clockwise and closed by rotating the actuator 7 anticlockwise Materials of the valve and particularly the plastics material of the "plastic to plastic" seal are suitable to withstand the rigours of the sterilisation process required in this field so that upon cooling of the valve the parts of the valve and the integrity of the seal upon sterilisation remain unaffected.

Still referring to FIGS. 1 to 7, the valve 1 is shown coupled to an opening 205 of a first external vessel or pipe 201 via flanges 54 of the first end 16 of the housing 5 and 254 of the opening 205. The flange 54 of the housing 5 comprises a coupling surface 215 alignable with a coupling surface 216 of the flange 254 of the vessel or pipe 201. The flange 54 of the valve 1 and the flange of the pipe or vessel 201 have matching endless grooves 202 formed on the coupling surfaces 215 and 216 of the flanges 54 and 254 respectively. When the valve 1 is in the closed state, the coupling surface 215 of the flange 54 and the end surface 21 of the plug 18 form a sterilisable external surface of the valve 1. An identical flange 54 is provided at the second end 161 of the housing 5 for mounting about an opening of a second vessel or pipe (not shown). A second external vessel or pipe is located at a fixed distance from the first vessel or pipe 201. This fixed distance is equal to the distance between coupling surfaces of flanges 54 of the housing 5.

A sealing washer 203 is placed intermediate the coupling surfaces 215 and 216 to sealingly couple them together. The sealing washer 203 comprises an expanded formation 203a (FIGS. 1 and 5) at the periphery of the sealing washer 203 which assists locating the sealing washer 203 in the grooves 202 and in use sits in the grooves 202. The flange 54 of the housing 5 of the valve 1 and the flange 254 of the vessel or pipe 201 and the sealing washer 203 placed therebetween can be secured together using a suitable fixing means such as a triclover clamp mechanism (not shown).

FIGS. 18 to 23 show the housing 5 of the first embodiment of the valve 1. The housing 5 is provided by a substantially hollow tube having a pair of parallel spaced apart guide rails 6 extending laterally from the external surface of the housing 5. The guide rails 6 encircle the housing 5 normal to the longitudinal axis of the housing 5. The actuator 7 is rotatably mounted on the portion of the housing 5 defined between the guide rails 6. Four recesses 212 (two shown in FIG. 21) are formed on the surface of the housing 5 between the guide rails 6 for receiving protrusions 81 of the actuator 7 (see FIGS. 31 and 34). The purpose of the recesses 212 and the protrusions 81 will be described below.

FIG. 17 shows a housing 50 for use with a second embodiment of the valve. This embodiment will be described in more detail with reference to FIGS. 41 and 42. The housing 17 is similar to the housing 5, and the numerals indicating the same features of the housing 5 are also used for the housing 50. The housing 50 differs from the housing 5 in that it is provided with a flange 56 at the second end 161 of the housing 50.

FIGS. 22 and 23 show grooves 202 formed in the coupling surfaces 215 of the flanges 54 of the housing 5.

FIGS. 24, 25, 28 and 29 show the piston 9 of the valve 1.

The piston 9 has two pairs of spaced apart annular slots 41, 42 formed around the external surface of the piston 9 perpendicular to the direction of travel of the piston 9. One pair of slots 42 is disposed adjacent the first end 17 of the piston 9 and the other pair of slots 41 is disposed adjacent the second end 53 of the piston 9. Both pairs of slots 41, 42 are formed for receiving O-rings (not shown) to prevent fluid flowing in a space between the internal surface of the housing 5 and the external surface of the piston 9. A pair of diametrically opposing bores 44 are formed intermediate the ends 17, 53 of the piston 9. These bores 44 are formed for engagement with spigots 102 extending from the cam followers 10 (see FIGS. 36 and 38). Two through-apertures 46 extend between exterior and interior of the piston 9 adjacent first end 17. These through-apertures 46 allow fluid to flow from a first vessel or pipe 201 connected to the first end 2 of the valve 1 into the opening of the first end 16 of the valve 1 and into the internal bore 47 of the piston 9 when the first vessel or pipe 201 is connected to the valve 1 in the open state of the valve 1.

FIG. 26 shows a piston 19 which is similar to the piston 9 described above and same numerals are used for indicating features of the piston 19 which are common with the piston 9. The piston 19 differs from the piston 9 in that the piston 19 has a flange 554 which is the same as the flanges 54 described for the housing 5.

FIG. 27 shows a piston 29 which is similar to the piston 9 and same numerals are used for indicating common features with the piston 9. The piston 29 differs from the piston 9 in that the piston 29 has a barbed fitting 55 provided at the second end 53 of the piston 29. This barbed fitting 55 is suitable for connection to various tubes having a range of diameters.

Both the pistons 19 and 29 are adapted for use with the housing 50 in the second embodiment of the valve which will be described with reference to FIGS. 41 and 42.

Referring now to FIGS. 30 to 35 there is shown the rotatable actuator 7 which comprises two identical component halves 71 each of which comprises a C-shaped collar 72, a handle 73 extending radially from one end of the C-shaped collar 72 and a connector 74 extending from the other end of the C-shaped collar 72 perpendicular to a plane of symmetry common for the component halves 17 when assembled. The handle 73 of each component half 71 comprises a wall 96 facing the other component half 71 when assembled and a slot 75 provided in the wall 96 for receiving the connector 74 of the other component half 71. The slot 75 is formed by a space between two opposing faces 96a of the wall 96. When the two component halves 71 are assembled together the C-shaped collars 72 of the component halves 71 as shown in FIG. 35 define a central circular bore 77.

The connector 74 of each component half 71 (see FIG. 32) is provided with a pair of resilient prongs 91 of a fork. Each prong has an expanded head 95 and a narrower shaft 98 defining a shoulder 93 therebetween. When assembling the valve 1, the two component halves 71 are located around the housing 5 which has the piston 9 pre-loaded therein between the two guide rails 6 so that the connector 74 of one of the components halves 71 is in register with the slot 75 of the other component half 71. The component halves 71 are then pressed together. As the connectors 74 enter the slots 75, the expanded heads 95 of the connectors 74 are pressed together by the opposing faces 96a to allow them to pass through the slot 75. Once the heads 95 pass beyond the slot 75, they spread apart due to the resilience of the prongs 91 and the shoulders 93 snap onto edges 94 which define a boundary between each of the opposing faces 96a and the inner surface of the wall 96.

The internal curved surface 78 of the C-shaped collar 72 has the cam 8 protruding therefrom. One end of each cam 8 has a protrusion 81a free tip of which snap-fits into the recesses 212 (see FIG. 21) of the housing 5 when the actuator is mounted on the housing 5 and when the valve 1 is in the open or closed states. This provides a user with tactile confirmation that the valve 1 is open or closed. Both ends of each cam 8 have a stop 82 which cannot pass through the slot 101 of the corresponding cam follower 10 to prevent the actuator 7 from rotating beyond a predetermined angle.

FIGS. 36 to 39 show the cam follower 10 comprising a main body 100 having the slot 101 on one side and the spigot 102 on the opposing side of the body 100. The slot 101 is formed for receiving the cam 8 and the spigot 102 is formed for insertion into the bores 44 defined on the pistons 9, 19, 29 (see FIGS. 24 to 29).

The actuator 7 and the cam followers 10 are adapted for use with both the first and the second embodiments of the valve.

FIG. 40 shows the fixed length valve 1 in perspective. The valve 1 has a housing 5 and rotary actuator 7 and a piston 9 which is not visible as it is enclosed within housing 5.

Figure 41A:
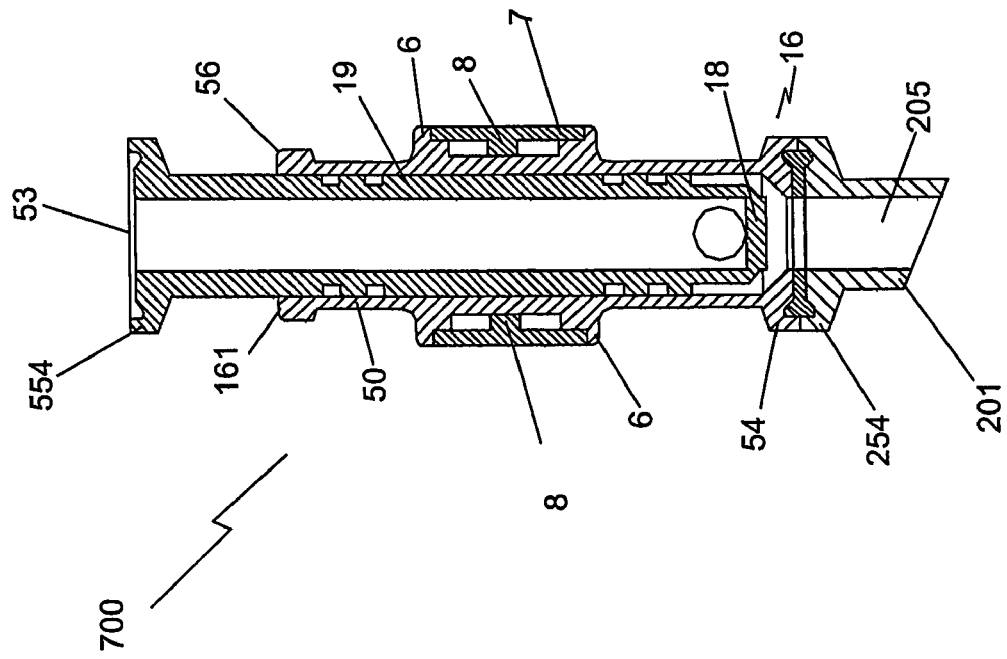
FIG. 41a is a sectional elevation of the valve of FIG. 41.
Figure 41:
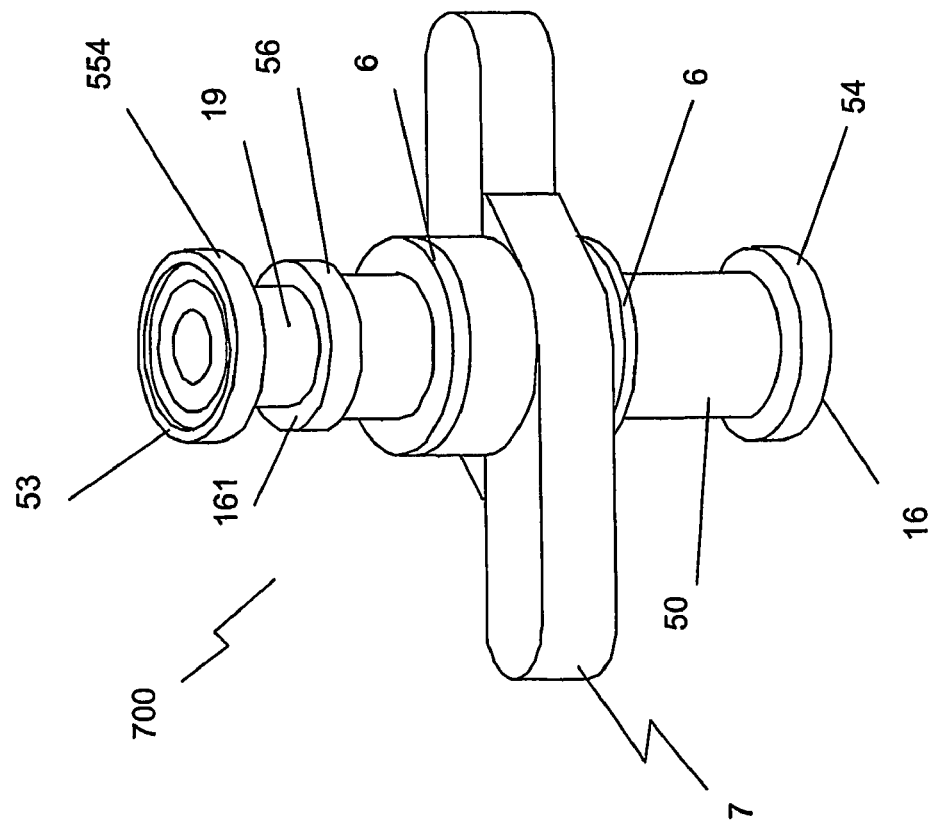
FIG. 41 is a perspective view of a second embodiment of the valve using the piston of FIG. 26.

FIGS. 41 and 41a show a second embodiment of the valve of the invention in perspective indicated generally by reference numeral 700. The valve 700 has an adjustable external length and is suitable for connecting flexible tubes or pipes. The valve 700 comprises the housing 50, the piston 19 and the actuator 7. The length of the valve increases as the piston 19 travels along the housing 50 from the closed position of the valve into the open position thereof and the second end 53 of the piston 19 extends outwardly from the second open end 161 of the housing 50. The flange 54 of the first end 16 of the housing 50 is connected to an opening of a first flexible tube or pipe (not shown) and the flange 554 of the piston 19, is connectable about an opening of a second flexible tube or pipe (not shown).

Figure 42A:
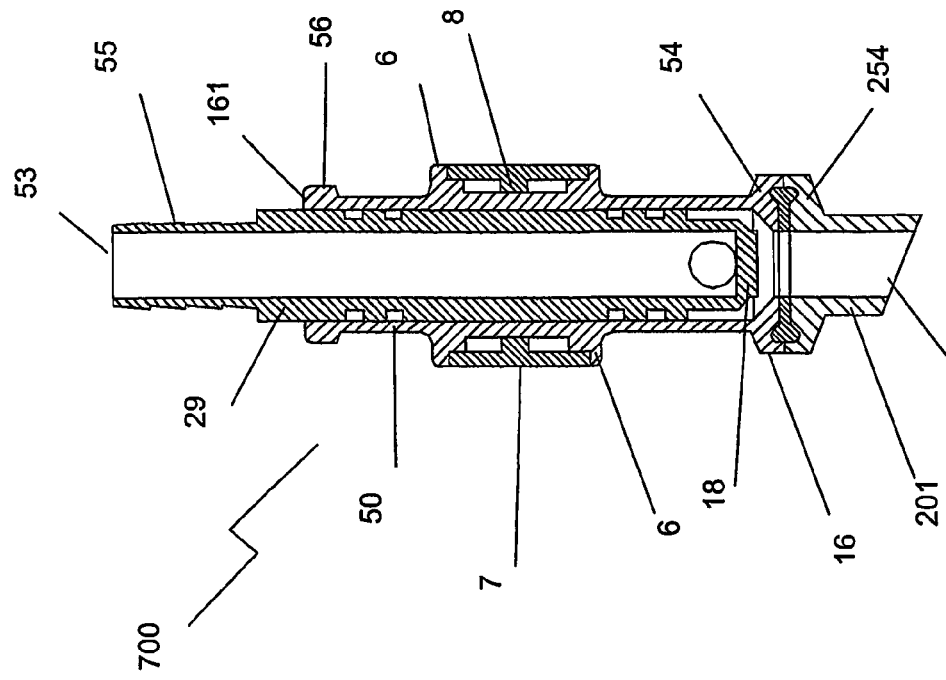
FIG. 42a is a sectional elevation of the valve of FIG. 42.
Figure 42:
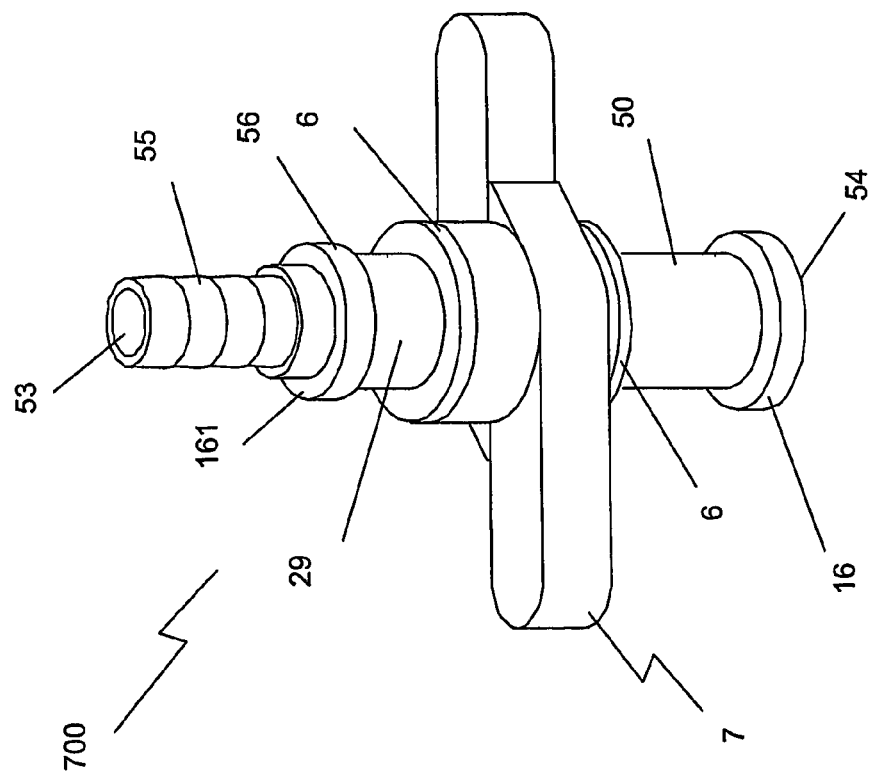
FIG. 42 is a perspective view of a second embodiment of the valve using the piston of FIG. 27.

FIGS. 42 and 42a show a valve 700 which uses a piston 29 instead of the piston 19. The barbed fitting 55 is connectable about an opening of a flexible tube or pipe which can have a range of diameters. The length of the valve increases as the piston 29 travels along the housing 50 from the closed position of the valve into the open position thereof and the second end 53 of the piston 29 extends outwardly from the second open end 161 of the housing 50. The flange 54 of the first end 16 of the housing 50 is connected to an opening of a first flexible tube or pipe (not shown) and the barbed fitting 55 of the piston 29 is connectable about an opening of a second flexible tube or pipe (not shown).

Referring now to FIGS. 8 to 16 there is shown a third embodiment of the valve of the invention indicated generally by reference numeral 121. The valve 121 comprises a housing 301 and a piston 309 disposed within the housing. The housing has a first end 340 and a second end 350. Sealing of the opening of the first end 340 of the housing 301 is formed in an identical way to that described for the valves 1 and 700 by means of a plug 180. The difference between the valve 1 and the valve 121 is that the valve 1 is operated by a rotary actuator 7 whereas the valve 121 is operated by a sliding actuator 117.

The valve 121 is a fixed length valve and serves the same purpose as described with reference to the valve 1. The housing 301 is connectable to openings of external devices disposed at a fixed distance from each other in the same way as described for the housing 5 of the valve 1.

The sliding actuator 117 of the valve 121 has a cam 118 along each of the opposing inner surfaces of side walls 305 and 306 of the sliding actuator 117.

The actuator 117 is slidably mounted on the housing 301. The cams 118 of the actuator 117 in use engage with respective cam slots 311 (FIG. 49) provided in the exterior of the piston 309 so that sliding of the actuator laterally relative the housing 301 between two end positions causes the cams 118 to co-operate with the cam slots 311 to enable translation of the piston along the longitudinal axis of the housing 301. The travel of the piston 309 occurs in the same manner as described with reference to the piston 9 of the valve 1. One end position of the sliding actuator 117 corresponds with an open state of the valve 121 and the other end position corresponds with a closed state of the valve 121. The cam slots 311 prevent rotation of the piston in the housing and permit only axial movement of the piston 309.

The housing 302 of FIG. 43 and the housing 301 of FIGS. 44 to 48 are similar to the housings 5 and 50 shown in FIGS. 17 to 23. Same numerals are used in the drawing for indicating same features of the housing 301 and 302. The housings 301 and 302 differ from the housings 5 and 50 in that two diametrically opposed slots 303, 304 are formed in the walls 310 of both housings 301, 302. The slots 303, 304 are formed for receiving the opposing side walls 305, 306 of the sliding actuator 117, (see FIGS. 56 to 60 for further details). Both slots 303, 304 have a lower shoulder 307 and an upper shoulder 308 between which the side walls 305, 306 of the sliding actuator 117 are received. Tracks 303a and 304a are formed in the walls 310 between the shoulders 307 and 308 in which the cams 118 of the actuator 117 slide.

The housing 301 has a flange 544 at both ends 340, 350 which are the same as the flanges 54 described for the housing 5 of the valve 1.

The housing 302 of FIG. 43 differs from the housing 301 in that it is provided with a flange 560 at the second end 350. The housing 302 is adapted for use with a fourth embodiment of the valve. The fourth embodiment of the valve will be described with reference to FIGS. 63 and 64.

FIGS. 47 and 48 show the flange 544 in detail.

FIGS. 49, 50 and 53 to 55 show the piston 309 of the valve 121. The piston 309 is similar to the piston 9 of the valve 1 except that the piston 309 has the two diametrically opposed cam slots 311 intermediate its first end 313 and second end 312. The cam slots 311 are defined by convex walls 315 which help to reduce friction during sliding motion of the actuator 117.

FIG. 51 shows a piston 319 which is similar to the piston 309 described above and same numerals are used for indicating features which are common with the piston 309. The piston 319 differs from the piston 309 in that the piston 319 has a flange 557 provided at the second end 312 which is the same as the flange 554 described for the piston 19 of the valve 700.

FIG. 52 shows a piston 329 which is similar to the piston 309 and same numerals are used for indicating common features with the piston 309. The piston 329 differs from the piston 309 in that the piston 329 has a barbed fitting 558 provided at the second end 312 which is the same as the barbed fitting 55 described for the piston 29 of the valve 700. Both pistons 319 and 329 are adapted for use with the housing 302 in the fourth embodiment of the valve as will be described with reference to FIGS. 63 and 64.

As shown in FIGS. 56 to 61 the sliding actuator 117 consists of two component halves 317, 318. One component half 317 has a pair of connectors 321 which are similar to the connector 74 as described with reference to FIG. 32. A pair of slots 322 is formed at corresponding locations in the other component half 318 of the sliding actuator 117.

When assembling the valve 121, the two component halves 317 and 318 are located around the housing 301 which has the piston 309 pre-loaded therein between the shoulders 307 and 308 of the housing 301 so that the connectors 321 of the component half 317 are in register with the slots 322 of the component half 318. The component halves 317 and 318 are then snap-fit together in a manner as described with reference to the component halves 71 of FIGS. 31 to 35. At the same time the cams 118 engage with the cam slots 311 of the piston 309.

Cams 118 have a substantially square cross-section (see FIGS. 10 and 14) and protrude from the internal surfaces of the side walls 305, 306. An end position retainer 331 is disposed centrally along the inner surface of each side wall 305, 306 adjacent each longitudinal edge 332 of the side walls 305, 306 of the component halves 317 and 318. These retainers provide tactile confirmation that the valve 121 is in an open or closed state. During transition of the valve 121 between open and closed states, as the actuator 117 slides between the shoulders 307 and 308 of the housing 301 from one end position to the other end position, the retainers 331 firstly engage with the outer surface of the housing 301 and slide over the outer surface of the housing 301 or 302 as the actuator 117 approaches the other end position. Upon the actuator 117 reaching the other end position, the retainers 331 snap off the outer surface of the housing 301 or 302 thus providing an indication that the valve 121 is open or closed.

The sliding actuator 117 is adapted for use with both the third and the fourth embodiments of the valve.

Figure 62:
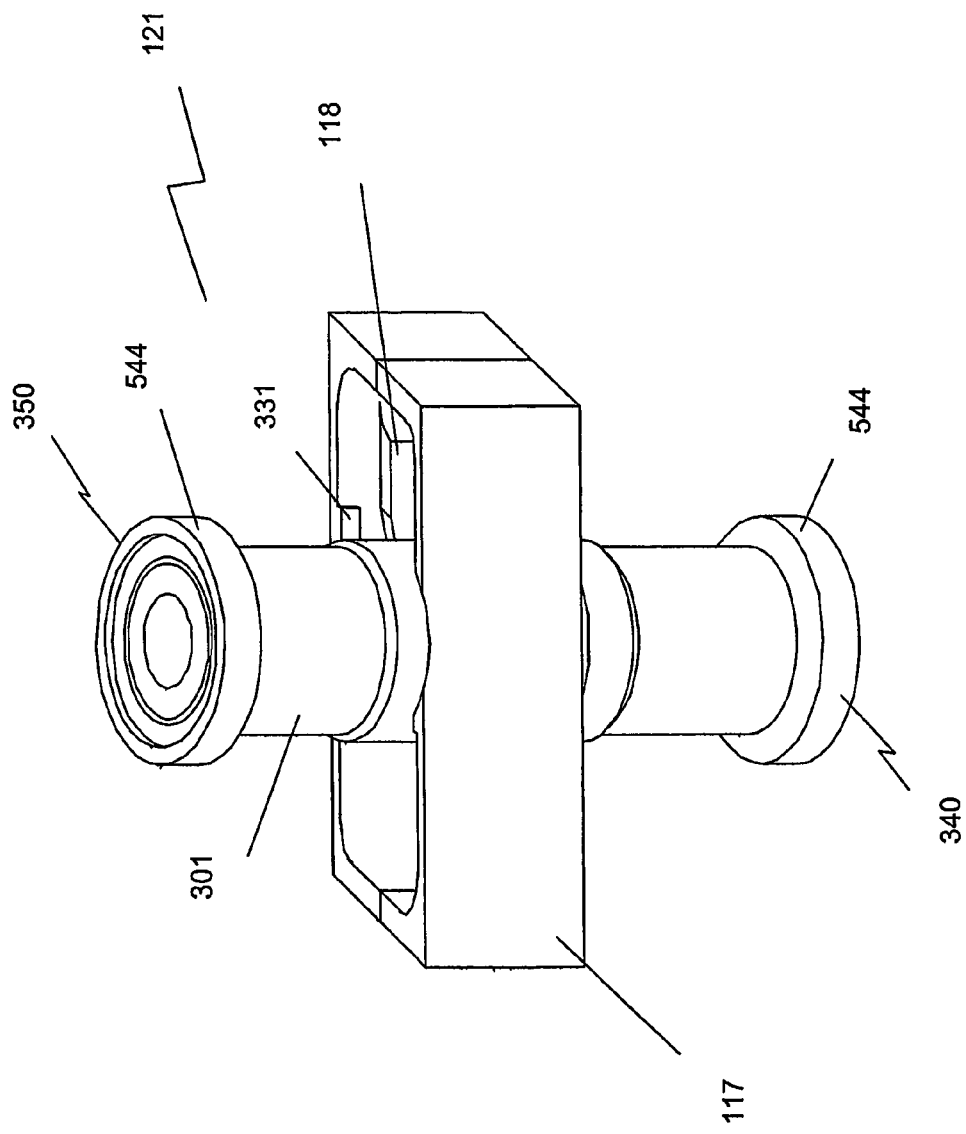
FIG. 62 is a perspective view of a third embodiment of the valve of the invention.

FIG. 62 shows a fixed length valve 121 having a housing 302, a sliding actuator 117 and a piston 309 which is not visible as it is enclosed within housing 302. The travel of the piston 309 within the housing 302 occurs in the same manner as described for the piston 9 with reference to the valve 1.

Figure 63:
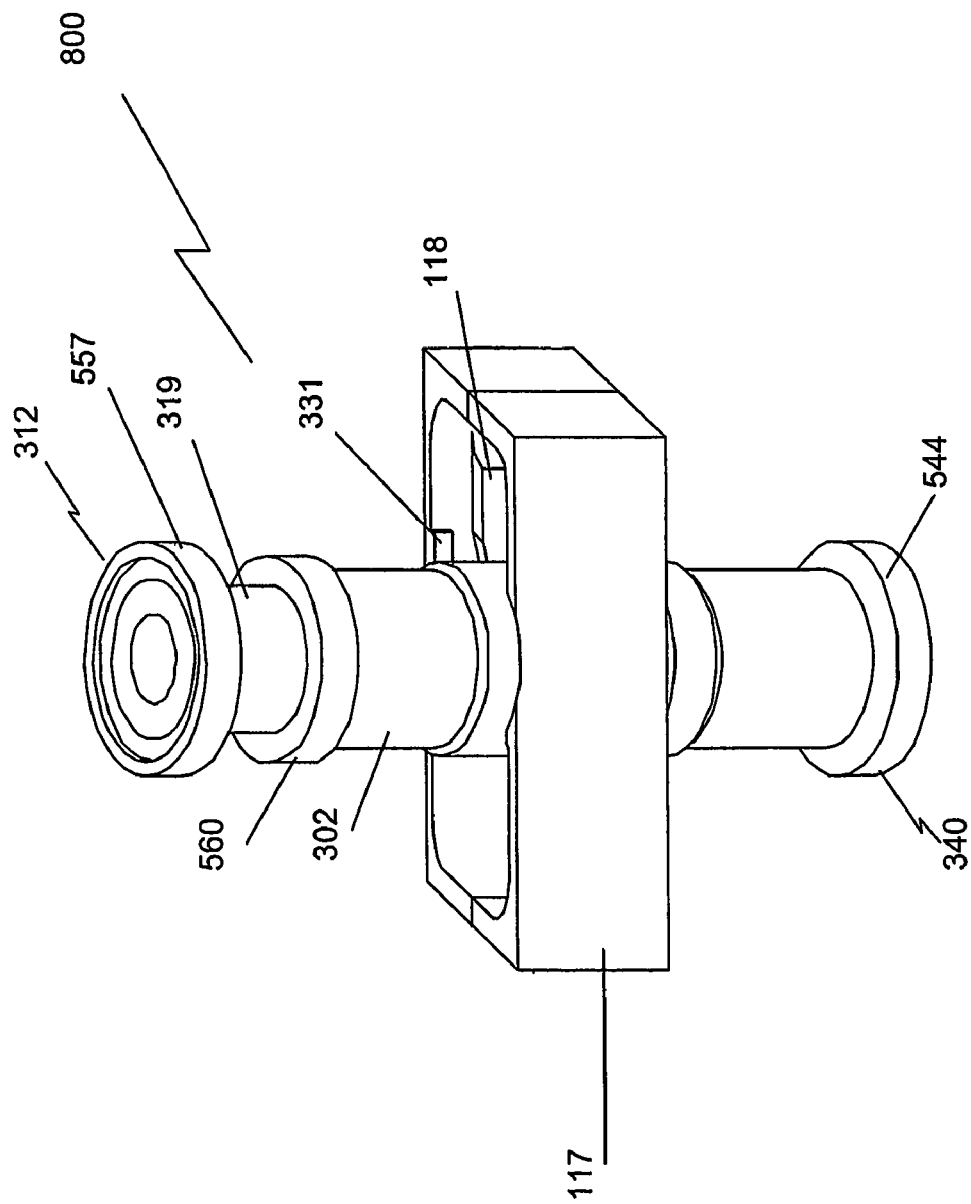
FIG. 63 is a perspective view of a fourth embodiment of the valve using the piston of FIG. 51.

FIG. 63 shows a fourth embodiment of the valve indicated generally by reference numeral 800 which has an adjustable external length. The valve 800 serves the same purpose as the valve 700 and comprises the housing 302, the piston 319 and the sliding actuator 117. The length of the valve 800 increases as the piston 319 travels along the housing 302 from the closed position into the open position of the valve and the second end 312 of the piston 319 extends outwardly from the end 350 of the housing 302. The flange 557 of the piston 319 is connectable about an opening of one flexible tube or pipe (not shown) and the flange 554 of the first end 340 of the housing 302 is connectable about an opening of an other flexible tube or pipe (not shown).

Figure 64:
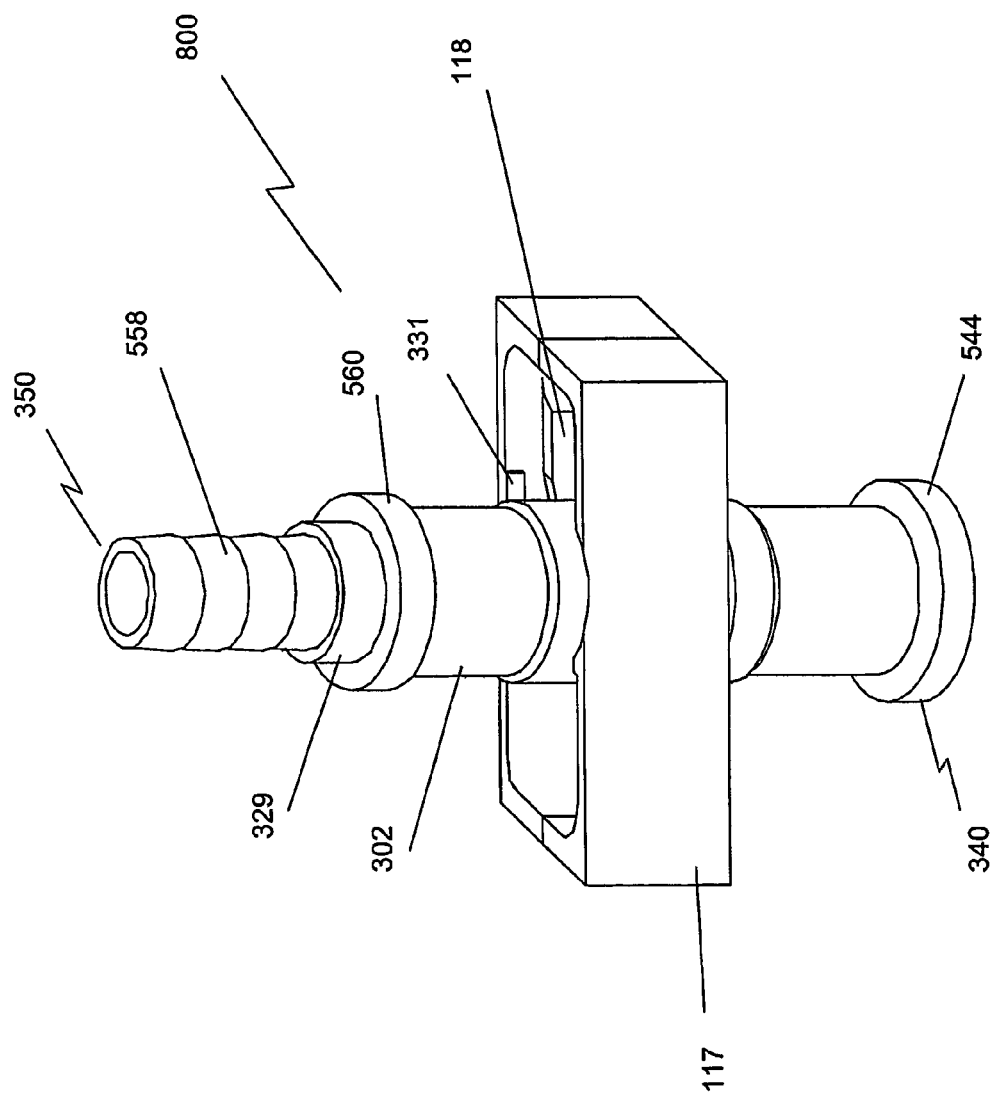
FIG. 64 is a perspective view of a fourth embodiment of the valve using the piston of FIG. 52.

FIG. 64 shows a valve 800 which uses a piston 329 instead of the piston 319. The barbed fitting 558 of the piston 329 is connectable to one flexible tube or pipe (not shown) which can have a range of diameters and the flange 554 of the first end 340 of the housing 302 is connectable about an opening of the other flexible tube or pipe (not shown).

Figure 66:
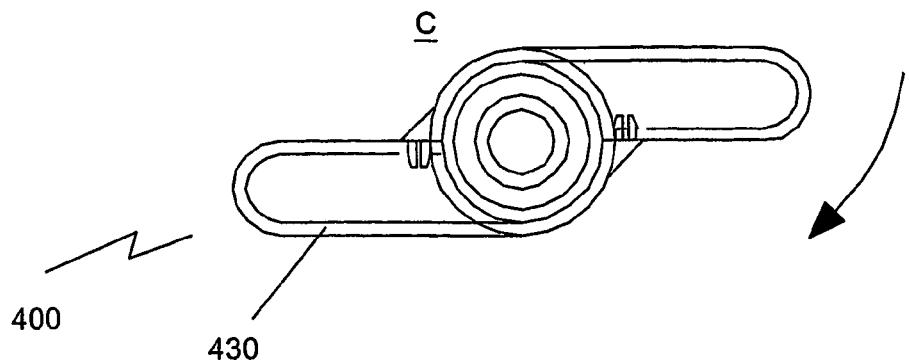
FIG. 66 is a bottom view of the valve of FIG. 65 in the direction of arrow C.
Figure 65:
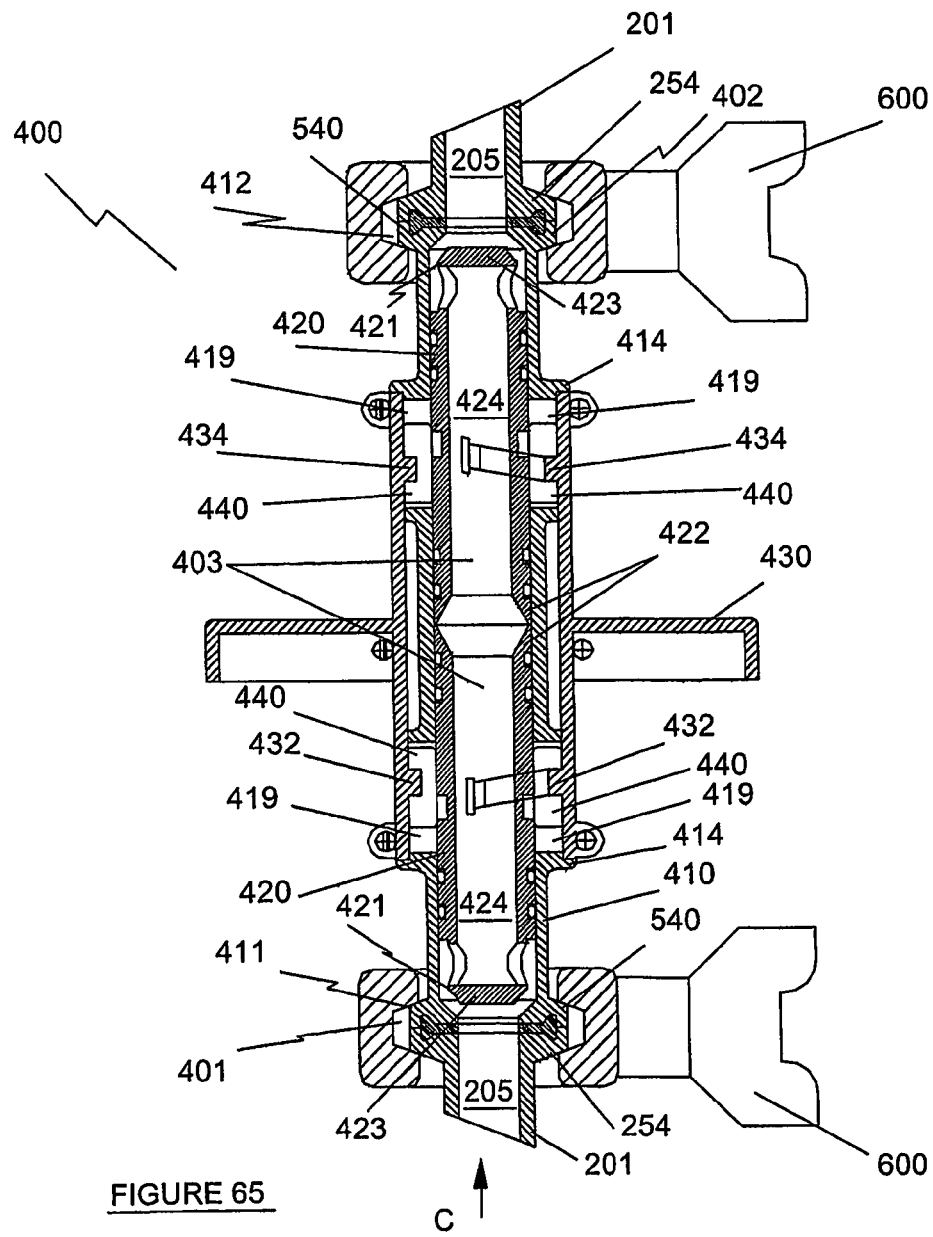
FIG. 65 is a sectional elevation of a fifth embodiment of the valve in an open position.
Figure 67:
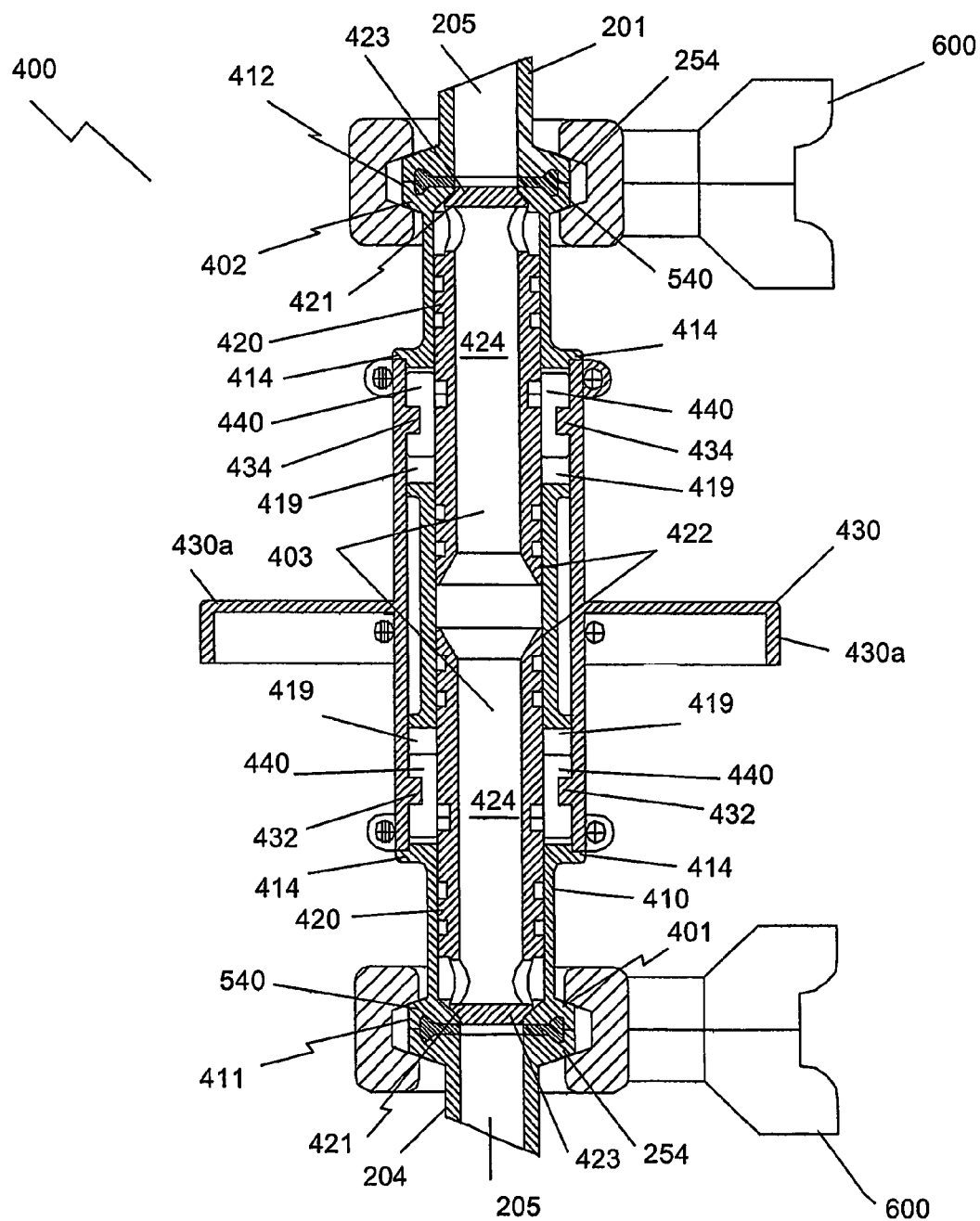
FIG. 67 as a sectional elevation of the valve of FIG. 65 in a closed position.

Referring to FIGS. 65, 66, and 67, there is shown a fifth embodiment of the valve according to the invention. The valve is indicated generally by reference numeral 400. The valve 400 has a body having first and second open ends 401, 402 and a passageway 403 extending between the ends.

The body of the valve 400 comprises a hollow tubular housing 410 and an actuator 430 rotatably mounted around the exterior the housing 410. Transition between open and closed states of the valve 400 is performed by rotating the actuator 430. The housing 410 has a first end 411 and a second end 412 and the actuator 430 has a first end 431 and a second end 433 and a pair of handles 430a.

The valve 400 is a fixed length valve and serves the same purpose as the valve 1 of FIGS. 1 to 7. The valve 400 is shown coupled to openings 205 of the vessels or pipes 201 via flanges 540 of the housing and flanges 254 of the vessels or pipes. The flanges 540 of the housing 400 and the manner of coupling the flanges 540 and 254 together are the same as described with reference to flanges 54 in FIGS. 1 to 7. The flanges 540 of the housing 410 of the valve 400 and of the vessels or pipes 201 can be secured together using a suitable fixing means such as a clamp device 600. The distance between coupling surfaces of the flanges 254 is fixed. This distance is equal to the distance between coupling surfaces of the flanges 540.

The valve 400 differs from the valve 1 in that a pair of pistons 420 is disposed within the housing 410 and the pistons 420 are operable to seal the openings of both the first and second ends 411 and 412 respectively of the housing 410 with plugs 423. The seal arrangement which blocks the openings of the first and second ends 411, 412 of the housing 410 is identical to the "plastic to plastic" seal described earlier with reference to the valves 1, 700, 121 and 800 of the invention. The pistons 420 are similar to the piston 9 of the valve 1. Each piston 420 has a first end 421 and a second end 422 and an internal bore 424 extending between the ends 421, 422. The pistons 420 are disposed in the housing 410 so that the second ends 422 face each other. The plugs 423 which form "plastic to plastic" seals with the openings of the first and the second ends 411, 412 of the housing 410 are provided at the first ends 421 of the pistons 420.

The actuator 430 further has a first pair of cams 432 on the inner surface of the actuator 430 proximal the first end 431 of the actuator and a second pair of cams 434 proximal the second end 433 of the actuator.

A cam follower 440 is mounted between each piston 420 and each cam 432 and 434 in through-slots 419 provided in the housing 410, so that the cam followers 440 are engaged with the cams 432, 434 and the pistons 420. Rotation of the actuator 430 causes the cams 432, 434 to co-operate with the cam followers 440 causing the cam followers 440 to travel along the through-slots 419 to enable simultaneous translation of both the pistons 420 along the longitudinal axis of the housing 410 for opening or closing of the valve. The through-slots 419 prevent rotation of the pistons 420 in the housing 410.

The travel of the pistons 420 within the housing 410 during transition of the valve 400 between open and closed states occurs so that no part of the pistons 420 extends outside the housing 410.

FIG. 65 shows the valve 400 in an open state. When the actuator 430 is rotated clockwise, as shown in FIG. 66, the piston 420 which is located proximal the first end 411 of the housing 410 together with the plug 423 is advanced towards the opening of the first end 411 of the housing 410, and the piston 420 which is proximal the second end 412 of the housing 410 together with the plug 423 is advanced towards the opening of the second end 412 of the housing 410 so as to bring the valve 400 into a closed state as shown in FIG. 67.

When the actuator 430 is rotated anticlockwise, the pistons 420 together with the plugs 423 move away from the openings of first and second ends 411, 412 of the housing 410 thus opening the valve 400 for passage of fluid in the same manner as described earlier with reference to the valve 1.

It will be appreciated that the actuator 420, the cams 432, 434, the housing 410, and the cam followers 440 can be mutually arranged so that the valve 400 is closed by rotating the actuator 430 anticlockwise and the valve 400 is opened by rotating the actuator 430 clockwise.

Figure 68:
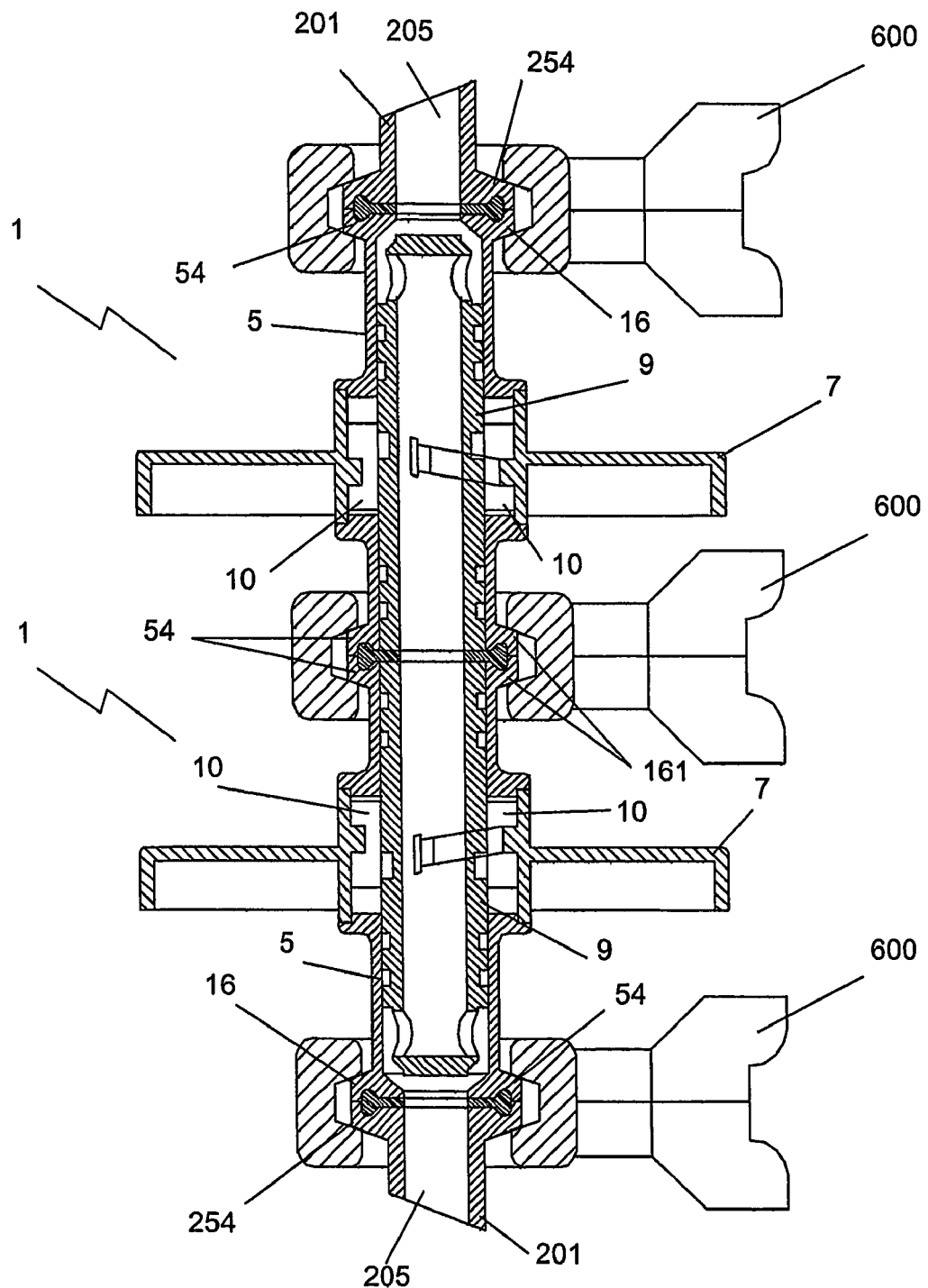
FIG. 68 is a sectional elevation of two valves of FIG. 6 coupled together with a clamp device.
Figures 72, 73:
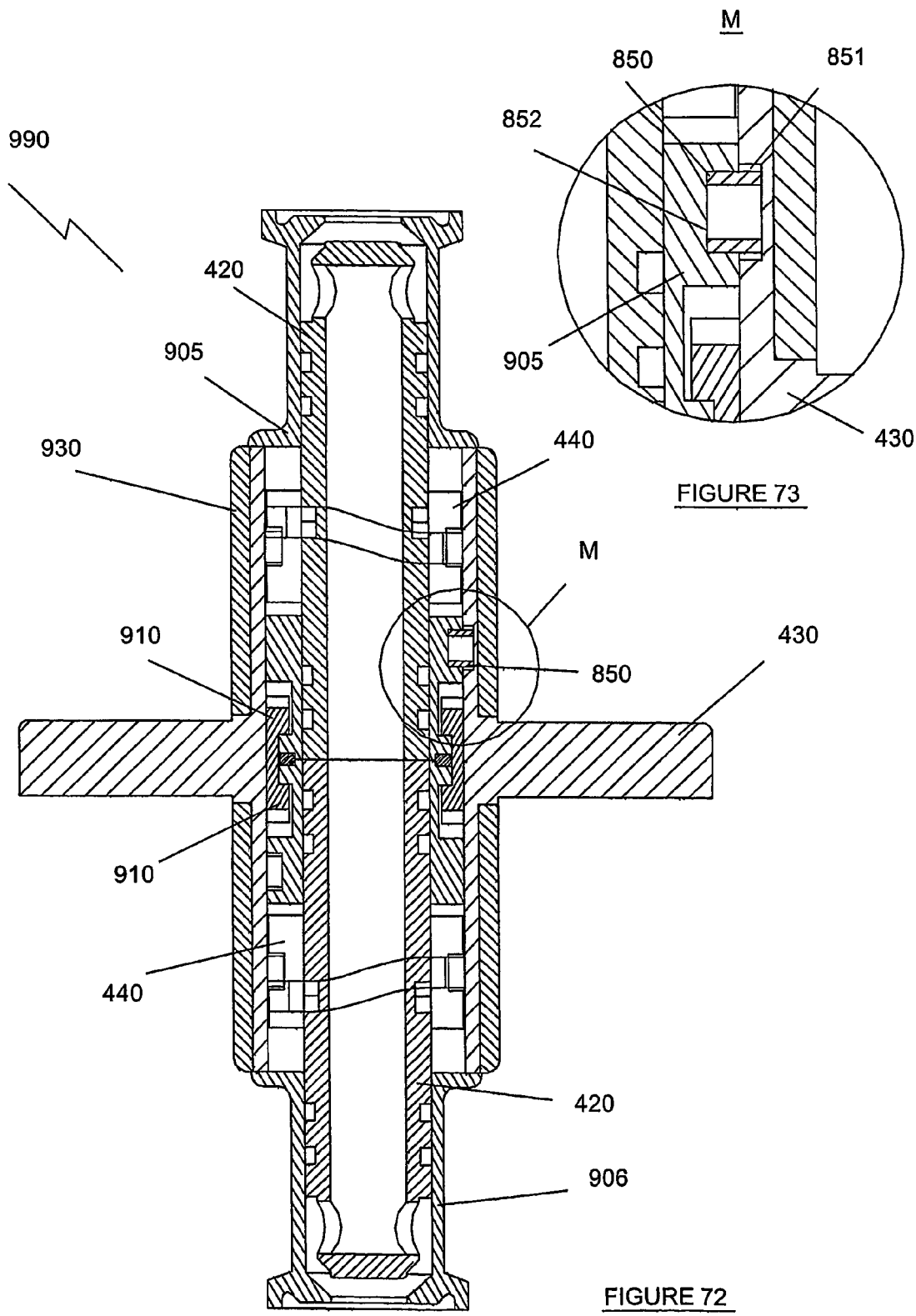
FIG. 72 is a cross-sectional elevation of a seventh embodiment of the valve in an open position.
FIG. 73 is an enlarged view of area M of FIG. 72.
Figure 75:
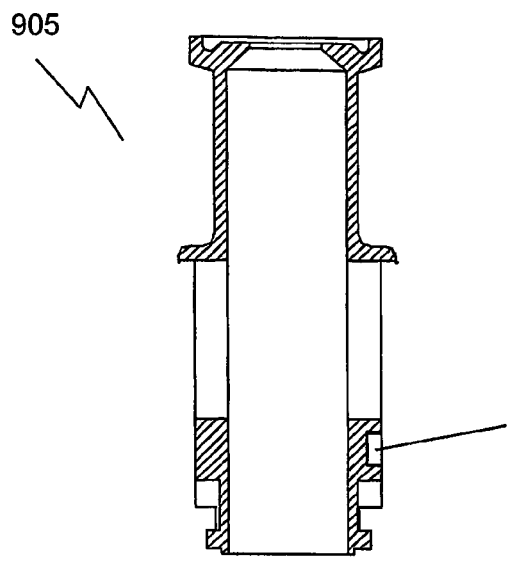
FIG. 75 is a cross-sectional elevation of a component half of a housing of the seventh embodiment of the valve.
Figure 76:
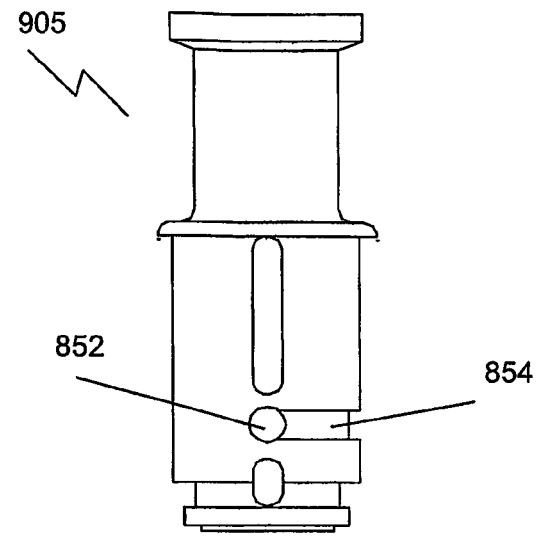
FIG. 76 is a front elevation of the housing of FIG. 75.
Figure 77:
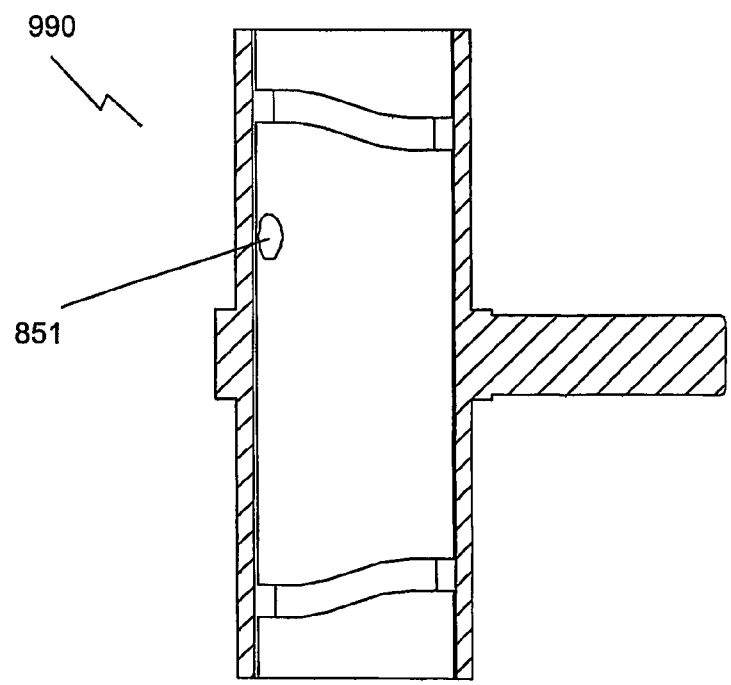
FIG. 77 is a cross-sectional elevation of a component half of an actuator of the seventh embodiment of the valve.

FIG. 68 shows two valves 1 sealingly coupled to each other via the flanges 54 at the second ends 161 of the housings 5 of the valves. The valves 1 are coupled to openings 205 of pipes or vessels 201 via the flanges 54 at the first ends 16 of the housings 5 and flanges 254 of the pipes or vessels 201. This arrangement allows both the first open ends 16 of the housings 5 to be sealed. This arrangement also allows consecutive opening or closing of the seals of the two valves 1. The valves 1 arranged in this manner are suitable for connecting two openings located at a fixed distance from each other. Of course, although not shown in the drawings, the valves 121 having sliding actuators 117 can be arranged in the same way and serve the same purpose, or indeed, a valve 1 can be coupled to a valve 121 in the same manner.

FIGS. 69 to 71 show a sixth embodiment of the valve of the invention indicated generally by reference numeral 900. The valve 900 is similar to the valve 400 and same numerals have been used to indicate features of the valve 900 which are the same as in the valve 400. The valve 900 differs from the valve 400 in that instead of the housing 410 the valve 900 has a housing comprising two component halves 905 and 906. The component half 905 comprises a first end 905*b* connectable to a pipe or vessel (not shown) via the flange 540 and a second end 905*c*. The component half 906 comprises a first end 906*b* connectable to a pipe or vessel (not shown) via the flange 540 and a second end 906*c*. The components halves 905, 906 are coupled to each other at the second ends 905*c*, 906*c* respectively by a clamp device comprising two identical parts 910 which hold the component halves 905, 906 together. Rotation of the assembled component halves 905, 906 relative to the clamp device is prevented by keys 905*a* and 906*a* of the component halves 905, 906 respectively engaged with corresponding slots (not indicated by a numeral) of the clamp device.

A sealing element such as an O-ring 915 is placed between end faces of the second ends 905*c*, 906*c* to provide a seal between the component halves 905, 906.

The handles 430*a* of the actuator 430 in this embodiment are provided with internal channels (not indicated by a numeral) with openings on the internal surface of the actuator 430. The channels are formed for receiving silicone springs 920 so that the springs 920 project from the internal surface of the actuator 430 and exert bias force on the clamp device, the component halves 905, 906 and the pistons 420 during actuations. The springs 920 provide tactile confirmation for a user that the valve is in the open or closed positions by snapping into respective cavities in the external surface of the clamp device upon completion of an actuation of the valve 900.

A cover 930 is placed around the exterior of the actuator 430 to provide extra hold for the assembly of the valve 900.

FIGS. 72 to 77 show a seventh embodiment of the valve of the invention indicated generally by reference numeral 990. The valve 990 is similar to the valve 900 and same numerals have been used to indicate features of the valve 990 which are the same as in the valve 900. The valve 990 differs from the valve 900 in that instead of silicone springs 920 used in the valve 900, an elastically deformable bushing 850 is placed intermediate the internal surface of the actuator 430 and the external surface of each component half 905, 906 of the housing for tactile confirmation for a user that the valve 990 is in the open or closed positions (see FIG. 73). Each bushing 850 is received in a cavity 851 formed in the inner surface of the respective actuator 430 at one end. A pair of angularly spaced-apart cavities 852 (one shown) are formed in the external surface of the respective component half 905, 906 at the other end. The cavities 852 are bridged by a groove 854 and the diameter of the cavities is greater than the width of the groove 854. In the open state of the valve 990 (FIGS. 72, 73) the other end of the bushing 850 is received in one of the cavities 852. During actuation of the valve 990, as the actuator 430 rotates relative to the housing, the bushing 850 exits the cavity 852 and travels along the groove 854 towards the other cavity 853 in a deformed state. Upon the valve 990 reaching the closed state, the bushing 850 snaps into the other cavity 852 and regains its shape. The operation is reversed during transition of the valve 990 from the closed into the open state.

In the fifth, the sixth and the seventh embodiments of the valve, the actuator 430 can be modified to enable independent actuation of the pistons 420 so that one end of the valve can be opened while the other end remains closed and vice versa. The actuator 430 can be replaced by a sliding actuator, such as a suitably modified sliding actuator 117.

In the first, the second, the fifth, the sixth and the seventh embodiments of the valve a 90 degree rotation of the respective actuators suffices for opening or closing of the valves. However, the cams of the actuators may allow for any other angle of rotation for opening or closing of these valves.

The valves according to the invention may be single use valves. Alternatively, and even more preferably, the valves may be multiple use valves and in particular, may be repeatedly opened and shut in situ in the line in which they are incorporated. This enables the valves to facilitate the operation of those processes in which a sample of product is desired to pass through the line from time to time. In order for a valve of the invention to be a multiple-use valve, sterility should be maintained in the interior of the valve during actuations. In order to achieve this, the valve can be provided with at least a pair of seal means disposed between the internal surface of the housing and the external surface of the piston with the seals of the pair being spaced apart from each other along the longitudinal axis of the valve at a distance which is greater than the distance of travel of the piston within the housing between open and closed states of the valve. The seal means should further be disposed within the valve so that in a closed state of the valve both seal means are located in the sterile interior of the valve; and in an open state of the valve one of the seal means is located in a non-sterile area of the valve whereas the other seal means remains in the sterile interior of the valve. An O-ring or any other suitable seal can be used as the seal means.

The above described valves are pre-assembled in the open state so that the curved surfaces of the plugs of the pistons are not engaged with the respective sharp rims of the open ends of the valves. The valves are then actuated in use to bring them into the closed state. This ensures that engagement of the curved surface areas of the plugs with the respective sharp rims occurs only as a consequence of the linear motion of the plugs towards the respective open ends. It is considered to be important to ensure that no rotational movement of the curved surface relative to the sharp rim can occur when the valve is closed or closely approaching the closed state. Such rotational motion should be avoided since it could cause relative stretching between the elements which provide the seal and this could comprise the seal itself.

The preferred material for the above-described embodiments of the valve of the invention is plastics material. However, other materials can be used for manufacturing valve parts other then the seal portions, such as for example metal.

In accordance with another aspect of the invention, other known valves, using known types of seals movable by a displacement means and modified so that the distance between the first and the second ends of the body of the valve remains unchanged during actuations of the valve may be utilised. Such valve may either have one seal for blocking one open end of the valve, or a pair of seals for blocking both the open ends of the valve (double-ended valve).

Figure 78:
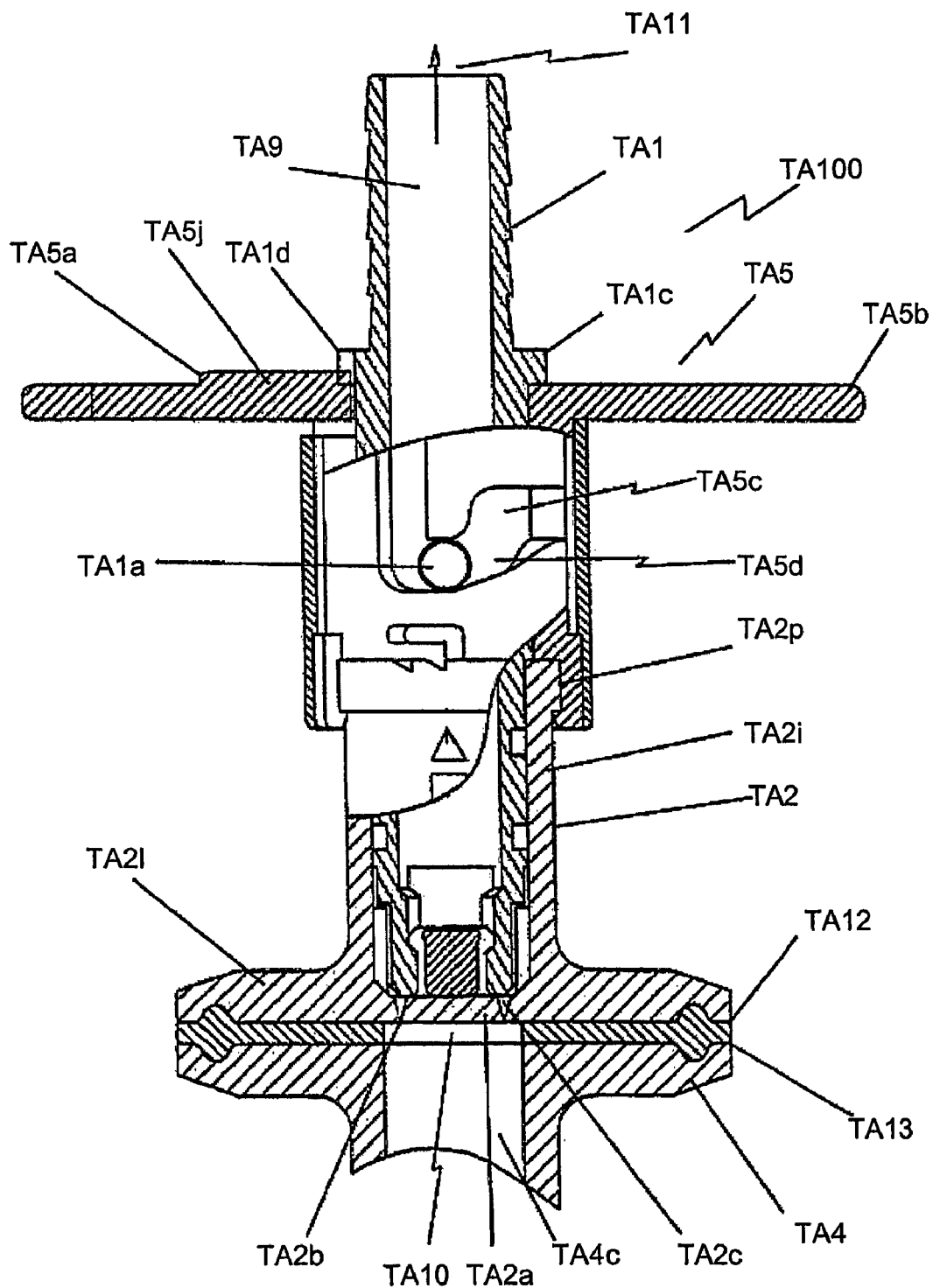
FIG. 78 is a cross-sectional elevation of a "tear-away" valve hot in accordance with the invention.

As an alternative linearly displaceable seal suitable for modification as a fixed length valve and/or a double-ended valve, FIG. 78 shows an "adjustable length" valve TA100 having a "tear-away" seal, such as described in published International Patent Application No. WO b 03/090842. Although shown in its "adjustable length" version, it will be apparent from the foregoing description of fixed length and double-ended valves that the "tear away" valve can be modified to convert it to a fixed-length and/or double ended version. The valve TA100 comprises a housing TA2 having a bore for receiving a hollow piston TA1. The valve TA100 has an entry side generally designated TA10 and an exit side generally designated TA11. At the entry side, the housing TA2 is connectable to a vessel TA4 so that a fluid path of the opening TA4c in the vessel TA4 and a fluid path TA9 of the valve TA100 are in register. Each of the housing TA2 and the vessel TA4 have corresponding mating surfaces TA12, TA13. The housing TA2 is formed with a sleeve region TA2i having at one end a flange TA2l. The base of the flange TA2l comprises the mating surface TA12. At its other end, the sleeve region TA2i is provided with a collar TA2p. At its exit side TA11, the piston TA1 extends from the valve TA100 and is couplable to a downstream process, tubing, piping, vessel or the like.

An actuator TA5 is connected to the housing TA2 by the collar TA2p and interconnects the piston TA1 and the housing TA2 with the locking mechanism TA5a. The actuator TA5 also comprises a handle TA5b by means of which the valve TA100 may be moved between open and closed states. Depending from handle TA5b is a cam mechanism TA5c for enabling the piston to be displaced longitudinally relative to the housing TA2 and the actuator TA5. The cam mechanism comprises a cam slot TA5d formed in the wall of the actuator TA5. The slot is engaged in use with a cam follower TA1a projecting from the external surface of the piston TA1 so that rotation of the actuator TA5 causes the cam slot TA5d to co-operate with the cam follower TA1a thus enabling axial translation of the piston TA1 within the housing TA2.

The entry side of valve TA100 is blocked with a sterilisable seal TA2a. In this embodiment of the invention the seal TA2a is formed integrally and continually with the housing TA2.

The seal TA2a is also connected to the piston TA1. A junction TA2b between the flange TA2l and the seal TA2a is formed on the interior surface of the seal TA2a, the interior surface of the seal TA2a being that surface facing the piston TA1. The junction TA2b comprises a weakened point or a fracture line, formed for example by providing a reduction in thickness of the housing TA2 in the area TA2c. When the valve TA100 is activated the seal TA2a and the flange portion TA2l separate at junction TA2b to provide a fluid passageway through the valve TA100.

The valve TA100 is opened by releasing the locking mechanism TA5a and rotating the handle TA5b in a clockwise direction. The locking mechanism TA5a comprises a release clip mechanism formed integrally with the handle TA5b and includes a tongue TA5j. The piston TA1 has a flange TA1c with a recess TA1d. When the valve is closed the tongue TA5j engages in the recess TA1d thereby preventing rotation of the handle TA5b. To release the locking mechanism TA5a, an external pressure such as a thumb force is applied to the tongue TA5j to depress it thereby disengaging the tongue TA5j from the recess TA1d. The actuator TA5 is then free to rotate.

Rotation of the actuator TA5 causes the piston TA1 to move in the direction of the arrow in FIG. 78, which causes the seal TA2a to rupture at the fracture line TA2b since the piston TA1 and seal TA2a are interconnected in the manner described below. This effectively withdraws the piston TA1 and the seal TA2a into the sleeve region TA2i of housing TA2 away from the flange TA2l by a linear displacement thus removing the seal TA2a from its position blocking the mouth TA10 of the valve and thereby enabling fluid to gain entry into the valve TA100.

In accordance with yet another aspect of the invention, although not shown in the drawings, other known valves using known types of seals movable by a displacement means, including but not limited to the "tear-away" valve, can be modified so that the seal is provided at both the open ends of the valve. A displacement means may be provided separately for each seal so that both ends can be operated independently of one another.

It will of course be understood that the invention is not limited to the specific details as herein described, which are given by way of example only, and that various alterations and modifications may be made without departing from the scope of the invention as defined in the appended claims.

What is claimed is:

1. A valve (1, 121, 700, 800, 400, 900, 990) comprising a body having first and second open ends (2, 3) and a passageway (4) for fluid between the ends, the first end (2) including a first coupling means (54, 544, 540) for sealingly connecting the body about an opening (205) of a first external device (201) and a seal blocking an open area of the first end (2) which in use is placeable in register with the opening (205) of the external device (201), the valve (1, 121, 700, 800, 400, 900, 990) further including a seal displacement means movable within the body so as to interrupt the seal permitting fluid to pass along the passageway (4) between the ends (2, 3), the coupling means (54) and the seal presenting a sterilisable mating surface for sealingly mating with a mating surface (216) about the opening (205) in the first external device, wherein the seal is formed between a first plastics portion movable by the seal displacement means and a second plastics portion disposed about the open area of the first end of the valve, wherein one of the plastic portions has a protruding sharp rim (15) and the other plastics portion of the seal has a curved surface area (22);

wherein in the closed position of the valve (1, 121, 700, 800, 400, 900, 990), the sharp rim (15) is engaged with the curved surface area (22) and a portion of the curved surface area (22) is displaced by the sharp rim (15);

wherein the materials of the sharp rim (15) and the curved surface area (22) are elastically deforming to seal the opening of the valve (1, 121, 700, 800, 400, 900, 990)

wherein the second plastic portion comprises a wall defining a bore portion (13) having a cross-section converging towards the first end (2) of the valve (1, 121, 700, 800, 400, 900, 990) which in turn leads to a wall defining a bore portion (14) having a substantially uniform cross-section which is located adjacent the first end (2) of the valve, the boundary between the wall defining the converging bore portion (13) and the wall defining the substantially uniform cross-section bore portion (14) defining the sharp rim (15), the first plastic portion having a body portion (19) with a cross-section converging towards the first end (2) of the valve and leading to an end portion (20) with a uniform cross-section, the end portion (20) being adjacent the first end (20) of the valve in use and a transitional surface between the external surface of the body portion and the external surface of the end portion (20) of the first plastic portion defining the curved surface area (22); and wherein each of the wall defining the converging bore portion (13) and the wall defining the substantially uniform cross-section bore portion (14) is non-tangential with respect to any point of the portion of the curved surface area (22) which is displaced by the sharp rim (15).

2. A valve (1, 121, 700, 800, 400, 900, 990) as claimed in claim 1, wherein the engagement of the sharp rim (15) with the curved surface area (22) occurs during a linear motion of the sharp rim (15) relative to the curved surface area (22).

3. A valve (1, 121, 700, 800, 400, 900, 990) as claimed in claim 1, wherein the first plastic portion is integrally formed with the seal displacement means.

4. A valve (1, 121, 700, 800, 400, 900, 990) as claimed in claim 1, wherein the first plastic portion is provided by a plastic plug (18) integrally formed with the seal displacement means.

5. A valve (1, 121, 700, 800, 400, 900, 990) as claimed in claim 1, wherein the second plastic portion is integrally formed with the body of the valve.

6. A valve (1, 121, 700, 800, 400, 900, 990) as claimed in claim 1, wherein the curved surface area (22) has a predetermined radius.

7. A valve (1, 121, 400, 900, 990) as claimed in claim 1, in which the second end (3) of the body comprises a second coupling means (54, 544, 540) with a mating surface for sealingly connecting the body about an opening of a second external device.

8. A valve (1, 121, 400, 900, 990) as claimed in claim 7, in which the distance between the mating surfaces of the first and the second coupling means (54, 544, 540) remains unchanged during movement of the seal displacement means within the body between open and closed positions of the valve (1, 121, 400, 900, 990) so that in use the valve can connect mating surfaces about openings (205) of a first and a second external devices (201) separated by a distance equal to the distance between the mating surfaces of the body.

9. A valve (700, 800) as claimed in claim 1, in which the seal displacement means travels at least partially outside of the second end (3) of the body on actuation of the valve (700, 800).

10. A valve (700, 800) as claimed in claim 9, in which the displacement means comprise first and second ends (17, 53, 313, 312), the first end (17, 313) comprising the first plastic portion and the second end (53, 312) comprising a coupling means (554, 55, 557, 558) for sealingly connecting the displacement means about an opening (205) of a second external device (201).

11. A valve (1, 121, 700, 800, 400, 900, 990) as claimed in claim 1, including means (920, 850) for displaying to a user the actuation state of the valve.

12. A valve (1, 121, 700, 800, 400, 900, 990) as claimed in claim 1, in which the body comprises a hollow housing (5, 50, 301, 302, 410, 905, 906) extending between the first and the second open ends.

13. A valve (1, 121, 700, 800, 400, 900, 990) as claimed in claim 12, in which the seal displacement means comprises a piston (9, 19, 219, 309, 319, 329, 420) slidably movable within the housing, the piston having the first plastic portion formed at one end thereof.

14. A valve (1, 121, 700, 800, 400, 900, 990) as claimed in claim 1 comprising an operating means having an actuator (7, 117, 430) externally mounted on the body and movable between a first and a second end position, the actuator (7, 117, 430) being linked with the seal displacement means so that movement of the actuator (7, 117, 430) between the first and the second end positions causes the seal displacement means to translate along the passageway between open and closed positions.

15. A valve (1, 121, 700, 800, 400, 900, 990) as claimed in claim 14, in which the actuator (7, 117, 430) is linked with the seal displacement means via a cam pair.

16. A valve (1, 121, 700, 800, 400, 900, 990) as claimed in claim 1, in which at least one guide element (211, 311, 419) is provided in the valve to prevent rotational motion of the seal displacement means and to permit the seal displacement means to move only linearly in the passageway.

17. A valve as claimed in claim 1, in which a seal is provided at both the first and the second open ends of the body, each seal having a seal displacement means movably disposed within the passageway of the body so that the first and/or second ends may be sealed or opened.

18. A valve as claimed in claim 1, the valve further including a cam and follower arrangement for moving said seal displacement means comprising an actuator, positioned concentrically about said body and rotatable about the axis of said body and having a pair of shaped slots and a piston having a pair of opposing outwardly projecting pins wherein each of said outwardly projecting pins are cooperatively engaged within said shaped slots and wherein each of said shaped slots has a first section that is substantially parallel to the longitudinal axis of said piston and a second section that is curved in a direction substantially perpendicular to the longitudinal axis of said piston, the piston is provided with a first plastics sealing plug movable by the seal displacement means into sealing engagement with a second plastics portion disposed about the open area of the first end.

19. A valve as claimed in claim 18, wherein said first section contacts said pins from 0 to 56 degrees rotation of said actuator and said second section contacts said pins from 56 to 80 degrees rotation of said actuator.

20. A valve as claimed in claim 18 in which said actuator includes a safety lock means for preventing undesired movement of the seal displacement means.

21. A valve as claimed in claim 18 including visible or tactile indication means for indicating to a user the position of the valve between its ready and deployed states.

22. A valve as claimed in claim 18, wherein said seal displacement means includes a first and a second internal seal arranged concentrically between said body and said seal displacement means, and longitudinally between said first and second open ends, wherein said first and second seal are separated by a distance parallel to the longitudinal axis of said displacement means.

23. A valve as claimed in claim 22, in which said distance separating said first and second seal is greater than the distance the seal displacement means moves from the ready state to the deployed state.

24. A valve as claimed in claim 18, in which the piston moves non-rotationally relative to the housing to open or close the valve.

25. A valve as claimed in claim 1, said first end (2) including said first coupling means (54, 544, 540) having a first mating surface and said second end including a second coupling means (54, 544, 540) with a second mating surface, the first and the second coupling means (54, 544, 540) being sealingly mateable with mating surfaces about openings (205) of first and second external devices (201) respectively, the first mating surface and the seal presenting a sterilisable surface, wherein the distance between the first and the second mating surfaces of the valve remains unchanged during movements of the seal displacement means within the body.

26. A valve as claimed in claim 25, in which the body comprises a hollow housing (5, 301, 410, 905, 906) extending between the first and the second open ends.

27. A valve as claimed in claim 26, in which the seal displacement means comprises a piston (9, 309, 420) slidably movable within the housing (5, 301, 410, 905, 906).

28. A valve as claimed in claim 25 comprising an operating means having an actuator (7, 117, 430) externally mounted on the body and movable between a first and a second end position, the actuator (7, 117, 430) being linked with the seal displacement means so that movement of the actuator (7, 117, 430) between the first and the second end positions causes the seal displacement means to translate along the passageway between open and closed positions.

29. A valve as claimed in claim 28, in which the actuator (7, 117, 430) is linked with the seal displacement means via a cam pair.

30. A valve as claimed in claim 25, in which at least one guide element (211, 311, 419) is provided in the valve to prevent rotational motion of the seal displacement means and to permit the seal displacement means to move only linearly in the passageway.

31. A valve as claimed in claim 25 including means for displaying to a user the actuation state of the valve.

32. A valve as claimed in claim 25, in which a seal is provided at both the first and the second open ends of the body, each seal having a seal displacement means movably disposed within the passageway of the body so that the first and/or second ends may be sealed or opened.

33. A valve as claimed in claim 25, in which first and second seals are provided for removably blocking open areas of the first and the second ends, respectively, which in use are placeable in register with the openings (205) of the first and the second external devices (201), the valve (400, 900, 990) further including a pair of seal displacement means (420) movable within the body so as to interrupt at least one of the seals permitting fluid to pass along the passageway (403) between the ends, the first mating surface and the first seal presenting a first sterilisable surface, and the second mating surface and the second seal presenting a second sterilisable surface.

34. A valve (400, 900, 990) as claimed in claim 33, in which the body comprises a hollow housing (410, 905, 906) extending between the first and the second open ends.

35. A valve (400, 900, 990) as claimed in claim 34, in which the seal displacement means comprises a piston (420) slidably movable within the housing (410, 905, 906).

36. A valve (400, 900, 990) as claimed in claim 33 comprising an operating means having at least one actuator (430) externally mounted on the body and movable between a first and a second end position, the actuator (430) being linked with at least one of the seal displacement means so that movement of the actuator (430) between the first and the second end positions causes the seal displacement means to translate along the passageway (403) between open and closed positions.

37. A valve (400, 900, 990) as claimed in claim 36, in which the actuator (430) is linked with the seal displacement means via a cam pair.

38. A valve (400, 900, 990) as claimed in claim 33, in which at least one guide element (419) is provided in the valve to prevent rotational motion of the seal displacement means and to permit the seal displacement means to move only linearly in the passageway.

39. A valve as claimed in claim 33 including means for displaying to a user the actuation state of the valve.

40. A valve as claimed in claim 33, wherein the distance between the first and the second mating surfaces of the valve remains unchanged during movements of the seal displacement means within the body.

* * * * *